United States Patent [19]

Smith et al.

[11] Patent Number: 5,300,506
[45] Date of Patent: Apr. 5, 1994

[54] INDOLYLALKYL DERIVATIVES OF PYRIMIDINYLPIPERAZINE FOR TREATING VASCULAR HEADACHE

[75] Inventors: David W. Smith, Clinton; Frank D. Yocca, Killingworth; Joseph P. Yevich, Southington; Ronald J. Mattson, Meriden; Andrew Williams, Middletown, all of Conn.; Edward H. Ruediger, Greenfield Park, Canada

[73] Assignee: Bristol-Myers Squibb Company, New York, N.Y.

[21] Appl. No.: 960,063

[22] Filed: Oct. 13, 1992

Related U.S. Application Data

[63] Continuation-in-part of Ser. No. 680,208, Apr. 4, 1991, abandoned, which is a continuation-in-part of Ser. No. 546,122, Jun. 29, 1990, abandoned.

[51] Int. Cl.$^5$ .................. A61K 31/505; C07D 403/00
[52] U.S. Cl. ..................................... 514/253; 544/295
[58] Field of Search ...................... 514/253; 544/295

[56] References Cited

U.S. PATENT DOCUMENTS 3,188,313  6/1965  Archer .................................. 544/360
3,562,278  2/1971  Archer .................................. 544/360

FOREIGN PATENT DOCUMENTS 0354094  2/1990  European Pat. Off. .
2124210  2/1984  United Kingdom .
2162522  2/1986  United Kingdom .

OTHER PUBLICATIONS

AMA Drug Evaluations 6th Edition, 1986, pp. 239–253 W.B. Saunders Co., Philadelphia, Pa.

Primary Examiner—Marianne M. Cintins
Assistant Examiner—Catherine S. Scalzo
Attorney, Agent, or Firm—Richard P. Ryan

[57] ABSTRACT

A series of novel indol-3-ylalkyl derivatives of alkoxypyrimidinylpiperazines are disclosed as Formula I.

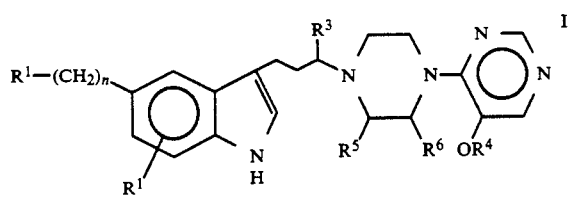

These compounds are intended to be useful agents for alleviation of vascular headache on the basis of their potent affinity and agonist activity at 5-HT1D binding sites.

18 Claims, No Drawings

INDOLYLALKYL DERIVATIVES OF PYRIMIDINYLPIPERAZINE FOR TREATING VASCULAR HEADACHE

CROSS REFERENCE TO RELATED APPLICATION

This is a continuation-in-part application of U.S. Ser. No. 07/680,208 filed Apr. 4, 1991 and now abandoned which is a continuation-in-part of U.S. Ser. No. 07/546,122, filed Jun. 29, 1990 and now abandoned.

BACKGROUND OF THE INVENTION

This invention generally pertains to heterocyclic carbon compounds having drug and bio-affecting properties and to their preparation and use. In particular the invention is concerned with 1,4-disubstituted piperazine derivatives wherein one substituent moiety is an indol-3-yl-alkyl group and the other moiety is an alkoxy-substituted pyrimidin-4-yl ring. These compounds possess a unique serotonergic profile that renders them useful in treatment of vascular headaches such as migraine.

Archer disclosed a large series of CNS-depressant indolylalkylpiperazines in U.S. Pat. No. 3,188,313. Among a large number of possible substituents on the 4-nitrogen atom of the piperazine ring was pyrimidine (unsubstituted). In U.S. Pat. No. 3,562,278, Archer disclosed and claimed a series of 1-indolylethyl-4-substituted-piperazines. Among the possible 4-substituents listed is 2-pyrimidinyl, again unsubstituted. The pharmacologic action disclosed for these art compounds is general CNS and psychomotor depression which bear no relationship to an antimigraine. Thus the compounds of Archer do not suggest the alkoxypyrimidine antimigraine compounds of this invention.

Dowie, et al. disclosed a series of 3-alkylaminoindole derivatives as being potentially useful for the treatment of migraine in a published patent application, GB 2,124,210. One member of this series of compounds was specifically claimed in a later patent application of Oxford, GB 2,162,522, published Feb. 5, 1986. This particular compound is known in the literature as sumatriptan.(1)

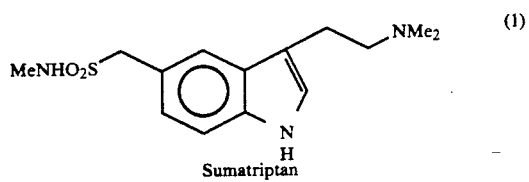

A series of novel indoline derivatives were disclosed Feb. 7, 1990 by Manoury, et al., in European patent application EPA 354,094. These compounds are described as being useful for treatment of various CNS disorders including depression, anxiety and migraine. Included among these art compounds are those of formula (2)

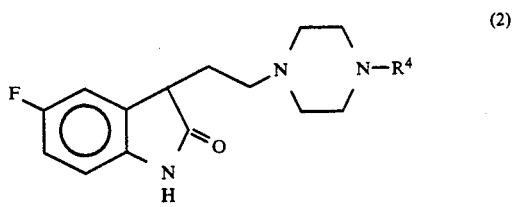

wherein $R^4$ is aryl, pyridine or quinoline moieties.

None of these art compounds make obvious the instant novel indol-3-ylalkyl derivatives of alkoxypyrimidinylpiperazine for treatment of vascular headaches such as migraine.

Migraine is a member of a broader class of headache which also comprises cluster headaches and other headaches believed to have a vascular implication in their etiology. These headaches are classified as vascular headaches. For a current summary of headache and its treatment see: Chapter 13: "Drugs Used to Treat Migraine and Other Headaches" in *Drug Evaluations*, 6th Edn., 1986, pages 239–253 American Medical Association, W. B. Saunders Co., Philadelphia, Pa.

Frequent irregularly-occurring episodes of headache afflict a large number of people but are usually acute in nature and of short duration. Relief of this type of headache is typically provided by mild analgesics such as aspirin or acetaminophen. Such headaches are quite common and, while painful and perhaps annoying, are seldom incapacitating and debilitating. Chronic recurrent headaches of the vascular category, however, usually lead to patient consultation with a physician due to pain severity which is often incapacitating.

Although there is no universally accepted classification system for headache, vascular headache, for the purposes of the present invention, refers mainly to migraine and cluster headaches. Migraine includes the common or classical type as well as migraine variants which would be familiar to one skilled in the art. Other subtypes such as toxic vascular and hypertensive headaches, chronic paroxysmal hemicrania, as well as some muscle-contraction and combined or mixed vascular-muscle headaches may also fall into a vascular-related headache category and be treatable by the present invention. It is appreciated by one skilled in the art that no single therapy is effective in all patients diagnosed with the same subtype of headache, thereby raising further uncertainties about headache classification.

Drugs most commonly used in treatment of headache fall into the following groups:
Ergot Alkaloids,
Beta-blocking Agents,
Calcium Channel Blocking Agents,
Antidepressants, and
Mixtures of these.

Management of recurring vascular headache is complicated by the lack of a single therapy which is effective in all patients with the same headache type and by the need to select either an abortive or prophylactic method of treatment for these headaches. Further complication involves the current use of drugs that cause dependence with extended use, such as ergotamine. Another important consideration for the present invention is that the more effective antimigraine agents in current use, e.g. the ergots, methysergide, produce severe use-limiting side-effects with long term usage.

Thus there is a need for a safe and effective drug for the treatment of migraine and related disorders which can be used either prophylactically or to alleviate an established headache.

The objectives of the present invention relate to the use of novel indol-3-ylalkyl derivatives of alkoxypyrimidinylpiperazines to provide treatment of vascular headaches, particularly migraine; to processes for their preparation; and to their pharmaceutical compositions and medical usage.

SUMMARY AND DETAILED DESCRIPTION OF THE INVENTION

The method of the present invention is intended for the alleviation of vascular or vascular-related headache of which migraine and cluster are the best known specific examples. The method essentially involves administration of an indol-3-ylalkyl derivative of alkoxypyrimidinylpiperazines, or a pharmaceutically acceptable salt and/or solvate thereof, to a human in need of such treatment. For use in the instant method, oral and transnasal administration of pharmaceutical compositions containing the subject antimigraine agents are preferred.

In a broad aspect, the present invention is concerned with treating vascular headaches with indol-3-ylalkyl derivatives of alkoxypyrimidinylpiperazines. A specific aspect concerns novel compounds having useful antimigraine serotonergic properties and characterized by Formula I

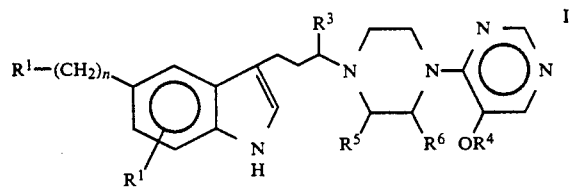

In Formula I, $R^1$ is a substituent selected from a group of substituents comprising hydrogen; halogen lower alkyl; lower alkoxy; phenyl-lower alkoxy, with the phenyl ring unsubstituted or bearing a lower alkyl substituent; amino; cyano; hydroxy; nitro; —OCH$_2$CN; —OCH$_2$CONR$^7$R$^8$; —SO$_2$NR$^7$R$^8$; —O$_2$CR$^9$; —SO$_2$R$^9$; —O$_2$CNR$^7$R$^8$; —COR$^8$; —CO$_2$R$^9$; —CONR$^7$R$^8$; —NR$^7$CO$_2$R$^9$; —NR$^7$COR$^8$; —NR$^7$SO$_2$R$^9$; and

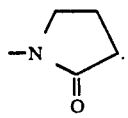

$R^2$ is selected from hydrogen, halogen, lower alkyl, lower alkoxy and —CO$_2$R$^9$.

$R^3$, $R^5$, $R^6$ and $R^7$ are independently selected from hydrogen and lower alkyl. $R^3$ however cannot be hydrogen when the $R^1$—(CH$_2$)$_n$ moiety is hydrogen, halogen, lower alkyl, lower alkoxy or —CONH$_2$ and $R^2$ is hydrogen, halogen or lower alkyl.

$R^4$ is lower alkyl.

$R^8$ is selected from hydrogen, lower alkyl, $R^7$-substituted phenyl-lower alkyl and trifluoromethyl.

$R^9$ is selected from lower alkyl and $R^7$-substituted phenyl-lower alkyl.

The symbol n is zero or the integers 1 or 2.

Additionally compounds of Formula I also encompass all pharmaceutically acceptable acid addition salts and/or solvates thereof. Hydrates are the preferred solvates. The present invention is also considered to include stereoisomers as well as optical isomers e.g. mixtures of enantiomers as well as individual enantiomers and diasteromers, which arise as a consequence of structural asymmetry in certain compounds of the instant series. Separation of the individual isomers is accomplished by application of various methods which are well known to practitioners in the art. The term "lower alkyl" refers to both straight and branched chain carbon radicals of from 1 to 4 carbon atoms inclusive. Illustrative of these radicals are carbon chains which can be methyl, ethyl, propyl, isopropyl, 1-butyl, 1-methylpropyl 2-methylpropyl.

Preferred compounds of Formula I are those wherein $R^1$ is a polar substituent attached to the 5-position of the indole ring.

The pharmaceutically acceptable acid addition salts of the invention are those in which the counter-ion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, fumaric, mandelic, oxalic, phosphoric, nitric, mucic, isethionic, palmitic, heptanoic, and others.

The compounds of Formula I can be prepared by adaptation of the general process shown in Scheme 1. Processes for syntheses of intermediate compounds are outlined in Scheme 2. In addition, certain compounds and their syntheses will be set forth in more detail in the Specific Embodiments section, infra.

SCHEME 1
GENERAL PROCESS FOR FORMULA I COMPOUNDS

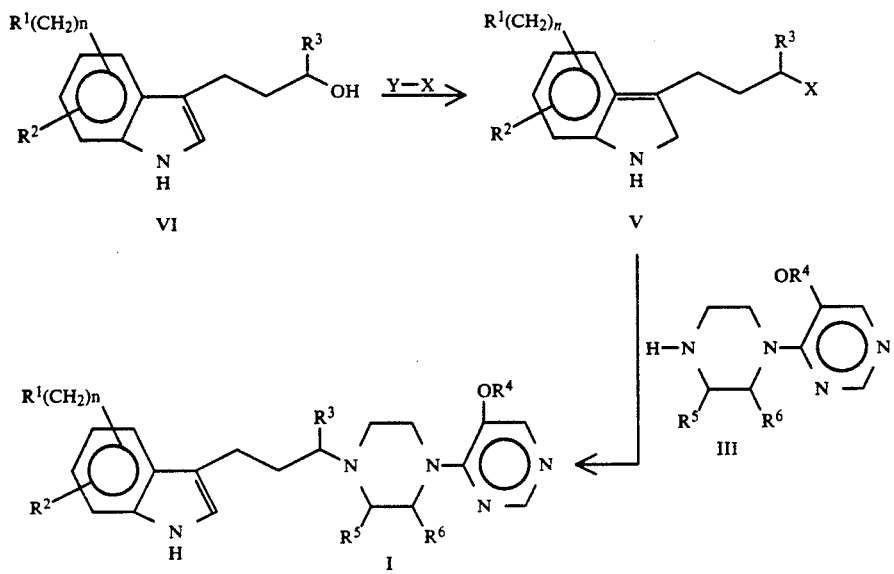

In the process of Scheme 1, $R^1$ through $R^6$ and n are as defined supra. The reagent Y-X represents an organic leaving group reagent wherein X is the leaving group fragment such as tosyl, mesyl, halide, sulfate, phosphate and so forth; and Y is either a proton or a counter ion: e.g. Y-X can be HBr, mesyl or tosyl chloride and the like. The reactions of Scheme I and their application are familiar to the practitioner skilled in organic synthesis and modifications of conditions and reagents would be readily understood.

An indolylalkyl alcohol of formula VI is converted to an activated intermediate of formula V in which the alcoholic moiety is converted into an organic leaving group. Reaction of intermediate V with a pyrimidinyl-piperazine of formula III then provides product I.

SCHEME 2
SYNTHETIC PROCESSES FOR INTERMEDIATE COMPOUNDS

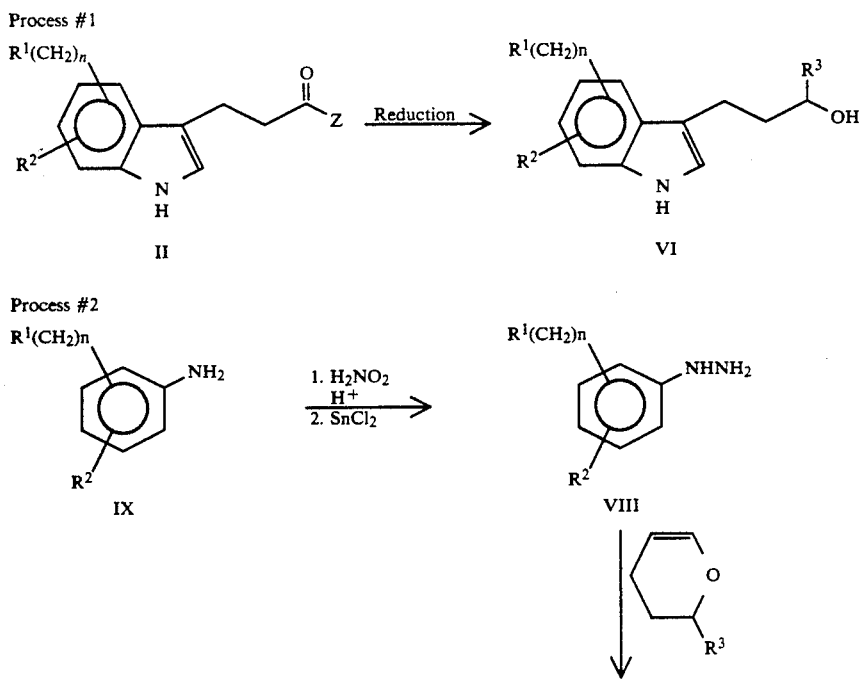

-continued
SCHEME 2
SYNTHETIC PROCESSES FOR INTERMEDIATE COMPOUNDS

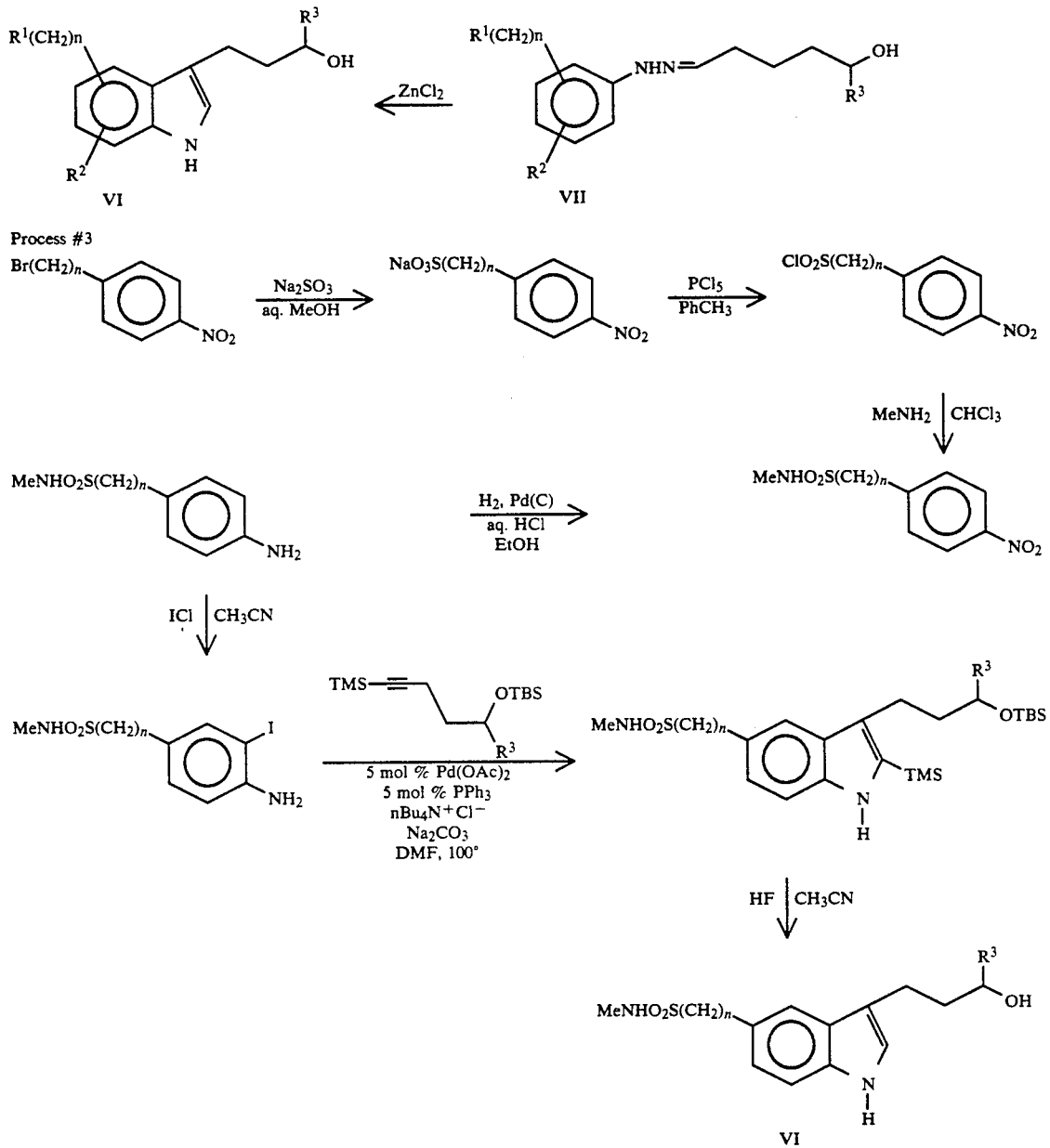

Scheme 2 sets out several processes for synthesis of Formula VI intermediates. Again the skilled synthetic chemist would know how to adapt these processes for preparation of specific Formula VI compounds. Process #1 symbolizes reduction processes in general for conversion of the compound II carbonyl moiety to the alcohol. Selection of reaction parameters would of course be dictated by the reactivity of $R^1$. The symbol Z is either lower alkyl, lower alkoxy or hydroxy. When Z is lower alkyl, $R^3$ in intermediate product VI will be lower alkyl.

A modification of process 1 can be done in conjunction with Scheme 1 by combining an appropriate compound of Formula II with a pyrimidinylpiperazine intermediate of Formula III followed by sodium cyanoborohydride treatment to produce the desired Formula I product. This is a desirable option for synthesizing products wherein $R^3$ is lower alkyl and $R^1$ is a moiety that is chemically inert to sodium cyanoborohydride.

Process #2 comprises synthetic elaboration of the indolylalkyl alcohol via the hydrazone intermediates VII and VIII followed by ring-closure to the indole system.

Process #3 sets out a particularly useful method for preparation of Formula VI intermediates wherein $R^1$ is —$SO_2NR^7R^8$. Specific examples comprising process #3 are given in detail in the experimental section, infra.

Additional formula I products can also be obtained by chemical conversions of the $R^1$-indolylsubstituent. Examples comprise conversion of the cyano group to the aminocarbonyl substituent by the action of strong hydroxide reagents such as KOH; conversion of amino groups to amides, lactams and sulfonamides as well as numerous conversions of an $R^1$ hydroxy substituent to other functional groups as shown in Scheme 4.

SCHEME 4
INDOLE FUNCTIONAL GROUP CONVERSION OF FORMULA I COMPOUNDS

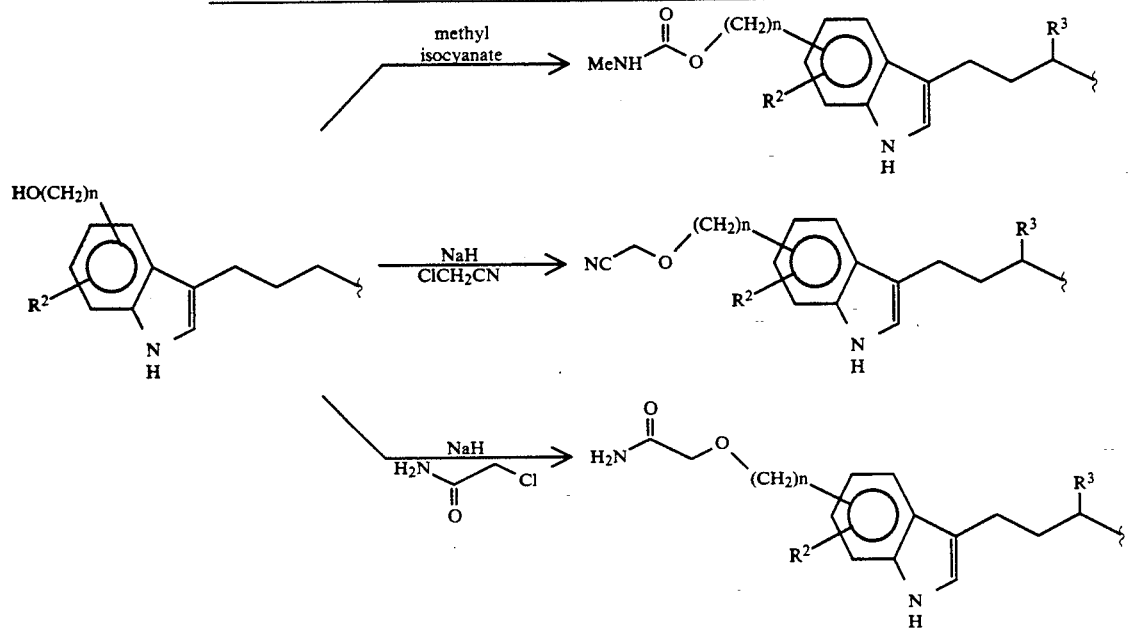

Reagents, solvents, and reaction conditions for the above described steps of these processes would be familiar to one skilled in organic synthesis as the processes comprise standard organic reactions, the details of which are readily available in the chemical literature. These processes may be adapted to variation in order to produce other compounds embraced by this invention but not specifically disclosed. Variations of the methods to produce the same compounds in somewhat different fashion will also be evident to one skilled in the art.

To provide greater descriptive detail, representative synthetic examples are provided hereinbelow in the "Description of Specific Embodiments" section.

Serotonin has been linked to the pathophysiology of migraine by accumulating evidence including increased excretion of serotonin metabolites following a migraine attack and a reduction in the serotonin content of blood platelets during the migraine headache. This latter effect appears to be specific for migraine and not a result of pain or stress. (Anthony, et al., "Plasma serotonin in migraine and stress", Arch. Neurol. 1967, 16: 544–552). More importantly, intramuscular injection of reserpine lowers plasma serotonin and induces a typical migraine-type headache in migraine sufferers. This induced headache can be alleviated by slow I.V. injection of serotonin creatinine sulfate. (Kimball, et al., "Effect of serotonin in migraine patients", Neurology N.Y.), 1960, 10: 107-111).

Although serotonin has been shown to be effective in treating migraine attacks, its use in migraine is precluded by its side-effects such as restlessness, nausea, faintness, hyperpnea, facial flushing and parasthesias. (Lance, et al., "The control of cranial arteries by humoral mechanisms and its relation to the migraine syndrome", Headache, 1967, 7: 93-102). For this reason more specific serotonin agents, which would treat the migraine without all of the other actions, are potentially useful antimigraine medicaments. Accumulating findings have led to the perception that compounds with selectivity for the 5-HT$_{1D}$ sub-type of serotonin receptors would be clinically efficacious in the treatment of migraine. In this regard the compounds of the instant invention demonstrate potent affinity and agonist activity at the 5-HT$_{1D}$ site. Formula I compounds of interest have potencies wherein IC$_{50}$ values of these compounds are less than 100 nmolar. Preferred compounds have IC$_{50}$ values below 10 nmolar.

Determination of 5-HT$_{1D}$ binding properties was accomplished employing methodology such as that described by Heuring and Peroutka, J. Neurosci., 7(3), 1987, 894-903; with only minor modifications. In vitro IC$_{50}$ (nM) test values were determined for the compounds of this invention employing tritiated serotonin.

Another aspect of the instant invention provides a method for treating a vascular headache sufferer which comprises systemic administration to the sufferer of a therapeutically effective amount of a compound of Formula I or a pharmaceutically acceptable salt and/or solvate thereof. Compounds of Formula XXI encompass additional compounds relating to Formula I compounds in that $R^3$ can be hydrogen regardless of the nature of $R^1$. Compounds of XXI are defined as

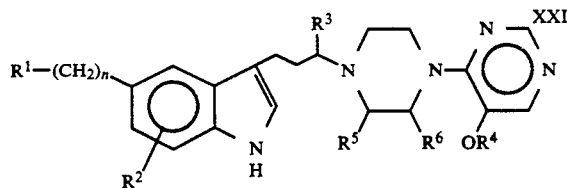

wherein
$R^1$ is a substituent selected from the group consisting of hydrogen, halogen, lower alkyl, lower alkoxy, $R^7$-substituted phenyl-lower alkoxy, amino, cyano, hydroxy, nitro, —OCH$_2$CN, —OCH$_2$CONR$^7$R$^8$, —SO$_2$NR$^7$R$^8$, —O$_2$CR$^9$, —SO$_2$R$^9$, —O$_2$CNR$^7$R$^8$, —COR$^8$, —CO$_2$R$^9$, —CONR$^7$R$^8$, NR$^7$CO$_2$R$^9$, —NR$^7$COR$^8$, —NR$^7$SO$_2$R$^9$ and

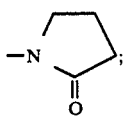

R$^2$ is selected from hydrogen, halogen, lower alkyl, lower alkoxy and —CO$_2$R$^9$;

R$^3$, R$^5$, R$^6$ and R$^7$ are independently selected from hydrogen and lower alkyl;

R$^4$ is lower alkyl;

R$^8$ is selected from hydrogen, lower alkyl, R$^7$-phenyl-lower alkyl and trifluoromethyl;

R$^9$ is selected from lower alkyl and R$^7$-phenyl-lower alkyl; and n is zero or the integers 1 or 2.

The administration and dosage regimen of compounds of Formula XXI is considered to be done in the same manner as for the reference compound sumatriptan, cf: Oxford, GB 2,162,522A. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably 0.1 to 2 mg/kg when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, intra-nasal, rectal and parenteral (i.e. intramuscular, intravenous and subcutaneous). Generally, it will be found that when a compound of the present invention is administered orally, a larger quantity of the active agent is required to produce the same effect as a smaller quantity given intra-nasally or parenterally. In accordance with good clinical practice, it is preferred to administer the instant compounds at a concentration level that will produce effective antimigraine effects without causing any harmful or untoward side effects.

The compounds of the present invention may be administered for antimigraine purposes either as individual therapeutic agents or as mixtures with other therapeutic agents. Therapeutically, they are generally given as pharmaceutical compositions comprised of an antimigraine amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for intra-nasal and parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not be construed as limiting the invention in sphere or scope. In the following examples, used to illustrate the foregoing synthetic processes, temperatures are expressed in degrees Celsius and melting points are uncorrected. The nuclear magnetic resonances (NMR) spectral characteristics refer to chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), triplet (t) or doublet (d). Abbreviations employed are DMSO-d$_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

The following examples describe in detail the preparation of compounds of Formula I, as well as synthetic intermediates in each process. It will be apparent to those skilled in the art that modifications, both of materials and methods, will allow preparation of other compounds disclosed herein. From the foregoing description and the following examples it is believed that one skilled in the art is able to use the invention to the fullest extent.

A. Preparation of Intermediate Compounds

Some representative procedures for preparation of synthetic intermediate compounds utilized in the three processes of Scheme 2 are given hereinbelow. Most starting materials and certain intermediates (e.g. Formula II and V compounds), are either commercially available or procedures for their synthesis are readily available in the chemical literature allowing their full utilization by one skilled in the art of organic synthetic chemistry.

Compounds of Formula VI

Compounds of type:

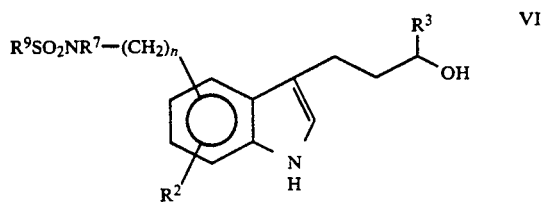

EXAMPLE 1

3-(5-Ethanesulfonylamino-1H-indol-3-yl)propanol

5-Ethanesulfonylamino-1H-indole

To a solution of 5-amino-1H-indole (10.0 g, 76 mmol) and triethylamine (15.8 mL, 114 mmol) in 100 mL $CH_2Cl_2$ at 0° C. was added dropwise a solution of ethanesulfonyl chloride (7.9 mL, 83 mmol) in 25 mL of $CH_2Cl_2$. The solution was allowed to slowly warm to 23° C. over 20 h. The reaction mixture was concentrated in vacuo and the residue dissolved in 400 mL of ethyl acetate. The organic layer was washed with 100 mL of water, 50 mL of 0.1M HCl, 50 mL of saturated $NaHCO_3$ solution, and 50 mL of saturated NaCl solution. The organic layer was dried over anhydrous $K_2CO_3$, filtered, and concentrated in vacuo to obtain 5-ethanesulfonylamino-1H-indole (16.9 g, >99%) which was used without further purification.

5-Methyl(ethanesulfonyl)amino-1H-indole

To a solution of 5-ethane-sulfonamino-1H-indole (8.96 g, 40 mmol) of in 200 mL of anhydrous THF at 0° C. was added dropwise a 2.5M solution of n-BuLi in hexane (17.6 mL, 44 mmol). After stirring for 30 minutes at 0° C., methyl iodide (6.25 g, 44 mmol) was added dropwise. The reaction mixture was allowed to warm to 23° C. and stir for 66 h. The mixture was poured into ethyl acetate, washed with five 100 mL portions of 1N NaOH, and, finally, with a saturated NaCl solution. The organic layer was dried over anhydrous $K_2CO_3$, filtered, and concentrated in vacuo to obtain 5-methyl(ethanesulfonyl)amino-1H-indole (9.52 g, >99%).

3-(5-Ethanesulfonylamino-1H-indol-3-yl)propanoic acid

A solution of 5-ethanesulfonylamino-1H-indole (8.0 g, 36 mmol), acrylic acid (5.15 g, 71 mmol), and acetic anhydride (7.3 g, 71 mmol) in 35 mL of acetic acid was heated at 90° C. for 20 h. The volatile materials were removed under high vacuum at 90° C. The remaining residue was dissolved in 1N NaOH and subsequently acidified to pH 1 with concentrated HCl. The aqueous solution was then extracted with five portions of ethyl acetate. The organic extracts were combined, dried over anhydrous $MgSO_4$, filtered, and concentrated in vacuo to yield 3-(5-ethanesulfonylamino-1H-indol-3-yl)propanoic acid (10.6 g of crude material). NMR and mass spectral analysis indicated the presence of the desired product. No attempt was made to purify this material; it was immediately subjected to reduction as described below.

3-(5-Ethanesulfonylamino-1H-indol-3-yl)propanol

To a solution of crude 3-(5-ethanesulfonylamino-1H-indol-3-yl)propanoic (10.6 g, 36 mmol) in 50 mL of THF at 0° C. was added a solution of 1.0M borane in THF (161 mL,161 mmol). The reaction mixture was allowed to warm to 23° C. and stand for two h. The reaction was cooled to 0° C. and 100 mL of 5N KOH was added slowly. After standing for 16 h, the organic layer was separated and the aqueous phase extracted with four portions of THF. The aqueous phase was neutralized with concentrated HCl and extracted with ethyl acetate. The combined organic layers were dried over anhydrous $K_2CO_3$, filtered, and concentrated in vacuo. Silica gel chromatography (95:5:0.5 $CH_2Cl_2$:MeOH:$NH_4OH$) of the residue afforded 3-(5-ethanesulfonylamino-1H-indol-3-yl)propanol (1.76 g, 18%)

Compounds of type

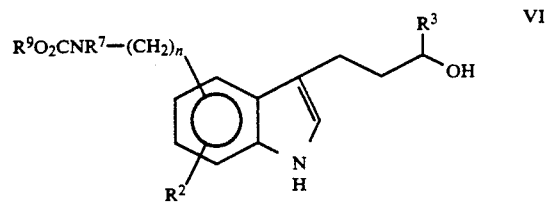

EXAMPLE 2

3-[5-(Phenylmethoxycarbonyl)amine]-1H-indol-3-yl]propanol

Phenylmethyl (1H-indol-5-yl)carbamate

To a solution of 5-aminoindole (10.0 g, 76 mmol) and triethylamine (7.67 g, 76 mmol) in acetonitrile (400 mL) at 0° C. was added dropwise a solution of carboxybenzyloxychloride (12.93 g, 75.8 mmol) in acetonitrile (80 mL). After the addition was complete the reaction was allowed to warm to 23° C. and stand for 60 h. The solvent was removed in vacuo and the residue treated with water containing $Na_2CO_3$ (76 mmol). The mixture was extracted with four portions of $CH_2Cl_2$. The combined organic extracts were washed with a saturated NaCl solution, dried with $K_2CO_3$, filtered, and concentrated in vacuo. Silica gel chromatography (4:1 to 1:1 hexane:ethyl acetate gradient) of the concentrate afforded phenylmethyl-(1H-indol-5-yl)carbamate (5.11 g, 25%).

Phenylmethyl [3-[(dimethylamino)methyl]-1H-indol-5-yl)carbamate

To a solution of phenylmethyl (1H-indol-5-yl)carbamate (3.76 g, 14.1 mmol) in ethanol (6 mL) was added dimethylamine (1.75 mL, 40% aq solution) and formaldehyde (1.25 mL, 40% aq solution). The reaction was heated at reflux for 16 h. The solvent was removed in vacuo and the residue treated with 10% $Na_2CO_3$ solution and extracted with four portions of ethyl acetate. The combined organic extracts were washed with saturated NaCl solution, dried with $Na_2CO_3$, filtered, and concentrated in vacuo. Silica gel chromatography (93:7:0.7 to 90:10:1 $CH_2Cl_2$:MeOH:$NH_4OH$ gradient) of the concentrate afforded phenylmethyl [3-[(dimethylamino)methyl]-1H-indol-5-yl]carbamate (2.30 g, 51%).

N,N,N-Trimethyl-1-[5-[(phenylmethoxycarbonyl)amine]-1H-indol-3-yl]methanaminium iodide To a solution of phenylmethyl[3-[(dimethylamino)methyl]-1H-indol-5-yl]carbamate (2.30 g, 7.1 mmol) in THF (75 mL) at 0° C. was added dropwise methyl iodide (1.52 g, 10.7 mmol). The reaction was allowed to warm to 23° C. and stand for 2 h. The precipitate was filtered and dried in vacuo to afford N,N,N-trimethyl-1-[5-[(phenylmethoxycarbonyl)amine]-1H-indol-3-yl]methanaminium iodide (2.94 g, 89%).

Methyl 2-methoxycarbonyl-3-[5-[(phenylmethoxycarbonyl)amine]-1H-indol-3-yl]propionate To a solution of sodium dimethyl malonate (1.12 g, 7.3 mmol) in MeOH (15 mL) was added a MeOH solution (50 mL) containing N,N,N-trimethyl-1-[5-](phenyl-methoxycarbonyl)amine]-1H-indol-3-yl]methanaminium iodide. The resulting solution was heated at reflux for 24 h. The solvent was removed in vacuo. The concentrate was treated with saturated NaHCO$_3$ and extracted with three portions of ethyl acetate. The combined organic extracts were washed with a saturated NaCl solution, dried with K$_2$CO$_3$, filtered, and concentrated in vacuo. Silica gel chromatography (60:40 hexane:ethyl acetate) of the concentrate afforded methyl 2-methoxycarbonyl-3-[5-[(phenylmethoxycarbonyl)amine]-1H-indol-3-yl]propionate (1.17 g, 59%) whose structure was confirmed by NMR and MS analysis.

Methyl 3-[5-[(phenylmethoxycarbonyl)amine]-1H-indol-3-yl]propionate

To a solution of methyl 2-methoxycarbonyl-3-[5-[(phenylmethoxycarbonyl)amine]-1H-indol-3-yl]-propionate (1.17 g, 2.8 mmol) in pyridine (15 mL) was added sodium iodide (0.83 g, 5.5 mmol) and the resulting solution heated at reflux for 24 h. The solvent was removed in vacuo. The concentrate was treated with saturated NaHCO$_3$ and extracted with four portions of ethyl acetate. The combined organic extracts were washed with a saturated NaCl solution, dried with K$_2$CO$_3$, filtered, and concentrated in vacuo. Silica gel chromatography (70:30 hexane:ethyl acetate) of the concentrate afforded methyl 3-[5-[(phenylmethoxycarbonyl)amine]-1H-indol-3-yl]propionate (0.47 g, 48%) whose structure was confirmed by NMR and MS analysis.

3-[5-[(Phenylmethoxycarbonyl)amine]-1H-indol-3-yl]propanol

To a suspension of LiAlH$_4$ (0.08 g, 2 mmol) in THF at −20° C. was added dropwise a THF solution (3 mL) of methyl 3-[5-[(phenyl-methoxycarbonyl]amine]-1H-indol-3-yl]propionate (0.47 g, 1.3 mmol). After the addition was complete, the reaction was allowed to stand at −20° C. for 5 h. The excess reducing agent was destroyed by the dropwise addition of water (0.1 mL), followed by 15% NaOH (0.1 mL), and, finally, 0.3 mL of water. The mixture was allowed to warm to 23° C. and stand for 16 h. The reaction was filtered through a pad of celite and the filter cake washed with Et$_2$O. The combined organic phases were dried with K$_2$CO$_3$, filtered, and concentrated in vacuo. Silica gel chromatography (1:1 hexane:ethyl acetate) of the concentrate afforded 3-[5-[(phenylmethoxycarbonyl)amine]-1H-indol-3-yl]propanol (0.31 g, 72%) whose structure was confirmed by NMR and MS analysis.

Compounds of type:

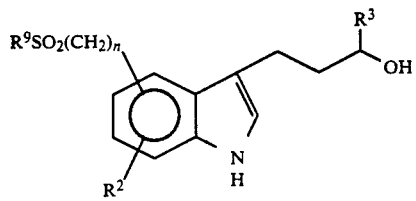

VI

EXAMPLE 3

3-[5[-(Methylsulfonyl)methyl]-1H-indol-3-yl]propanol
1-[2-(Methylsulfonyl)methyl]-4-nitrobenzene A solution of 4-nitrobenzyl bromide (2.16 g, 10 mmol) and sodium methanesulfinate (1.12 g, 11 mmol) in DMF (25 mL) was heated at reflux for 0.5 h. The solvent was removed in vacuo and the residue extracted with CH$_2$Cl$_2$ and water. The combined organic phases were washed with a saturated NaCl solution, dried over MgSO$_4$, filtered, and concentrated in vacuo to yield 1-[2-(methylsulfonyl)methyl]-4-nitrobenzene (1.54 g, 71.6%) which was used without further purification.

1-8 2-(Methylsulfonyl)ethyl]-4-nitrobenzene

This compound was prepared in a similar manner from 1-(2-bromoethyl)-4-nitrobenzene and sodium methanesulfinate.

4-Amino-1-[2-(methylsulfonyl)metyl]benzene

A suspension of 1-[2-(methylsulfonyl)methyl]-4-nitrobenzene (27 g, 126 mmol) and concentrated HCl (5 mL) in 300 mL of 66% ethanol (aq) was hydrogenated (50 psi) over 10% Pd/C catalyst (4 g) at 23° C. for 16 h. The catalyst was removed by filtration and the filtrate concentrated in vacuo to remove the ethanol. The remaining aqueous phase was made basic to litmus by addition of 50% NaOH whereupon the product, 4-amino-1-[2-(methylsulfonyl)methyl]benzene, precipitated (21.54 g, 93%).

1-[2-(5-Hydroxypentylidene)hydrazinyl]-4-[(methylsulfonyl)methyl]benzene

To a concentrated HCl solution (40 mL) of 4-amino-1-[(methylsulfonyl)methyl]benzene (8.0 g, 43 mmol) was added water (40 mL). The reaction was cooled to 0° C. and a solution containing NaNO$_3$ (3.58 g, 51 mmol) in water (10 mL) was added dropwise. The reaction was allowed to stir at 0° C. for one h and then poured into a solution of SnCl$_2$ (48.78 g, 216 mmol) in 6N HCl (160 mL) at −40° C. The reaction was allowed to warm to 23° C. and the pH then adjusted to 2 with 50% NaOH. Ethanol (300 mL) and dihydropyran (4.73 g, 56 mmol) were added and the reaction was stirred for 16 h. The mixture was made basic with 50% NaOH (pH=10) and then filtered over celite. The resulting solution was concentrated in vacuo and the remaining aqueous phase extracted with ethyl acetate. The combined organic layers were washed with water, dried with MgSO$_4$, filtered, and concentrated in vacuo. Silica gel chromatography (CH$_2$Cl$_2$:MeOH:NH$_4$OH; 95:5:0.5) of the concentrate afforded the desired hydrazone (4.34 g, 38%).

3-[5-[(Methylsulfonyl)methyl]-1H-indol-3-yl]propanol

A 1,2-dimethoxyethane solution containing 1-[2-(5-hydroxy-pentylidene)hydrazinyl]-4-[(methylsulfonyl)methyl]benzene (4.74 g, 17 mmol) and ZnCl$_2$ (11.4 g, 84 mmol) was heated at reflux for 24 h. The reaction was concentrated in vacuo and the residue dissolved in water and extracted with ethyl acetate. The combined organic layers were washed with water, dried with MgSO$_4$, filtered, and concentrated in vacuo. Silica gel chromatography (CH$_2$Cl$_2$:MeOH:NH$_4$OH; 95:5:0.5) of the concentrate afforded 3-[5-[(methylsulfonyl)methyl]-1H-indol-3-yl]propanol (1.23 g, 28%).

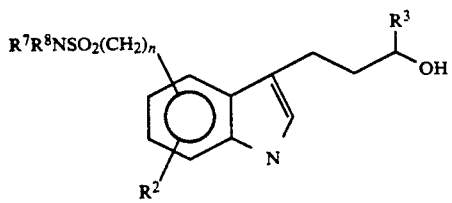

EXAMPLE 4

3-(3-Hydroxypropyl)-N-methyl-1H-indole-5-methanesulfonamide

4-[2-(5-Hydroxypentylidene)hydrazinyl]-N-methylbenzene methanesulfonamide

To a suspension of 14.0 g (69.9 mmol, 1.0 equiv.) of 4-((N-methyl methanesulfonamido)methyl)aniline in 140 mL of concentrated aqueous hydrochloric acid and 70 mL of water at 0° C. was added 4.82 g of sodium nitrite in 70 mL of water. The mixture was stirred for fifteen minutes at 0° C. Meanwhile a solution of 78.9 g of stannous chloride in 140 mL of concentrated aqueous hydrochloric acid was prepared and cooled to −45° C. The solution of the diazonium salt was filtered into the stannous chloride solution. The reaction was allowed to warm to 0° C. over the course of one hour and then carefully brought to pH 3.5 by the addition of solid potassium hydroxide. The reaction was diluted with 420 mL of ethanol and 7.65 mL (83.9 mmol, 1.2 equiv.) of 3,4-dihydro-2H-pyran was added. The reaction mixture was allowed to stir at room temperature for sixteen hours. The pH was further raised to 10 by the addition of solid potassium hydroxide. The mixture was filtered and ethanol was removed in vacuo. The remaining aqueous layer was extracted three times with 500 mL portions of ethyl acetate. The combined organic layers were dried over anhydrous sodium sulfate, filtered and concentrated to afford an oil. The oil was chromatographed on silica gel using 5% methanol in methylene chloride containing 0.5% concentrated aqueous ammonium hydroxide to obtain 7.85 g (38%) of 4-[2-(5-hydroxypentylidene) hydrazinyl]-N-methylbenzenemethane sulfonamide.

3-(3-Hydroxypropyl)-N-methyl-1H-indole-5-methanesulfonamide

To a solution of 23.6 g (173 mmol, 5.0 equiv.) of zinc chloride in 1000 mL of anhydrous 1,2-dimethoxyethane under a nitrogen atmosphere was added a solution of 10.37 g (34.65 mmol, 1.0 equiv.) of 4-[2-(5-hydroxypentylidene)hydrazinyl]-N-methylbenzenemethanesulfonamide in 200 mL of anhydrous 1,2-dimethoxyethane. The solution was heated to reflux for thirty hours. The reaction was cooled to room temperature and the volume concentrated to 500 mL in vacuo. The residue was diluted with 1000 mL of ethyl acetate and washed with 200 mL portions of water and saturated aqueous sodium chloride. The organic layer was dried over magnesium sulfate, filtered and concentrated in vacuo to yield an oil. The oil was purified by chromatography on silica gel using 5% methanol in methylene chloride containing 0.5% concentrated aqueous ammonium hydroxide to obtain 5.16 g (53%) of 3-(3-hydroxypropyl)-N-methyl-1H-indole-5-methanesulfonamide.

EXAMPLE 5

Alternate Synthesis (Via Scheme 2 Process #3)

4-Amino-3-iodo-N-methylbenzenemethanesulfonamide

To a suspension of 1.06 g (5.31 mmol, 1.0 equiv.) of 4-amino-N-methylbenzenemethanesulfonamide in 20 mL of acetonitrile was added 0.862 g (5.31 mmol, 1.0 equiv.) of iodine monochloride. The reaction was stirred for 15 minutes at room temperature. The mixture was partitioned between 25 mL of ethyl acetate and 15 mL of 20% aqueous sodium thiosulfate. The organic layer was dried over anhydrous sodium sulfate, filtered and concentrated in vacuo to yield an oil. The oil was filtered through a plug of silica gel using 40% ethyl acetate in hexane to yield 1.13 g (65%) of 4-amino-3-iodo-N-methylbenzenemethanesulfonamide

1-t-Butyldimethylsilyloxy-4-pentyne

To a suspension of 18.0 g (749 mmol, 1.05 equiv.) of sodium hydride in 500 mL of THF at 0° C. was added a solution of 60.0 g (713 mmol, 1.00 equiv.) of 4-pentyne-1-ol in 150 mL of THF. When the addition was complete the reaction was allowed to warm to room temperature over one hour. To this mixture was added 113 g (749 mmol, 1.05 equiv.) of t-butyldimethylsilyl chloride in 150 mL of THF. The reaction was allowed to stir for 16 hours at room temperature then diluted with 1200 mL of hexane. The organic layer was washed with 500 mL of saturated aqueous sodium bicarbonate, dried over anhydrous sodium sulfate and concentrated in vacuo. The resulting liquid was distilled at 39°–42° C. at 0.05 mm Hg to yield 135 g (96%) of 1-t-butyldimethylsilyloxy-4-pentyne

1-t-Butyldimethylsilyloxy-5-trimethylsilyl-4-pentyne.

To a solution of 135 g (682 mmol, 1.0 equiv.) of 1-t-butyldimethylsilyloxy-4-pentyne in 700 mL of THF at −78° C. was added 311 mL (716 mmol, 1.05 equiv.) of a 2.3M solution of n-butyllithium in hexane. The −78° C. bath was removed and the reaction temperature was monitored as it rose to 0° C. The reaction was recooled to −78° C. and 90.8 mL (716 mmol, 1.05 equiv.) of trimethylsilyl chloride was added dropwise. The reaction was then allowed to warm slowly in the cold bath for 16 hours. The reaction was diluted with 2000 mL of hexane, washed with 500 mL of saturated aqueous sodium bicarbonate, dried over anhydrous sodium sulfate and concentrated in vacuo. The resulting liquid was distilled at 71°–74° C. at 0.05 mm Hg to yield 168 g (91%) of 1-t-butyldimethylsilyloxy-5-trimethylsilyl-4-pentyne.

3-(3-t-Butyldimethylsilyloxypropyl)-2-trimethylsilyl-N-methyl-1H-indole-5-methanesulfonamide To a solution of 0.326 g (1.0 mmol, 1.0 equiv.) of 4-amino-3-iodo-N-methylbenzenemethanesulfonamide in 20 mL of dimethylformamide was added 0.541 g (2.0 mmol, 2.0 equiv.) of 1-t-butyldimethylsilyloxy-5-trimethylsilyl-4-pentyne, 0.278 g (1.0 mmol, 1.0 equiv.) of tetrabutylammonium chloride, 0.530 g (5.0 mmol, 5.0 equiv.) of sodium carbonate, 0.0131 g (0.05 mmol, 0.05 equiv.) of triphenylphosphine, and 0.0112 g (0.05 g, 0.05 equiv.) of palladium (II) acetate. The mixture was heated in a 100° C. oil bath for 16 hours. The mixture was cooled to room temperature and the dimethylformamide removed in vacuo. The residue was diluted with 75 mL of ethyl acetate and washed with 25 mL of saturated aqueous sodium bicarbonate. The organic layer was dried over anhydrous sodium sulfate, filtered and concentrated in vacuo to yield an oil. The oil was filtered through a plug of silica gel with 25% ethyl acetate in hexane to yield 0.411 g (88%) of 3-(3-t-butyldimethylsilyloxypropyl)-2-trimethylsilyl-N-methyl-1H-indole-5-methanesulfonamide.

3-(3-Hydroxypropyl)-2-trimethylsilyl-N-methyl-1H-indole-5-methanesulfonamide To a solution of 0.0738 g (0.157 mmol, 1.0 equiv.) of 3-(3-t-butyldimethysilyloxypropyl)-2-trimethylsilyl-N-methyl-1H-indole-5-methanesulfonamide in 2 mL of pyridine at 0° C. was added I mL of 48% aqueous hydrofluoric acid. The solution was stirred for 20 minutes at 0° C. The solution was diluted with 25 mL of ethyl acetate and washed with 10 mL of 10% aqueous sodium carbonate. The organic layer was dried over anhydrous sodium sulfate, filtered and concentrated in vacuo to yield 0.0551 g (99%) of 3-(3-hydroxypropyl)-2-trimethylsilyl-N-methyl-1H-indole-5-methanesulfonamide, homogeneous by $^1$H NMR and TLC.

3-(3=Hydroxypropyl)-N-methyl-1H-indole-5-methanesulfonamide

To a solution of 0.0551 g (0.155 mmol, 1.0 equiv.) of 3-(3-hydroxypropyl)-2-trimethylsilyl-N-methyl-1H-indole-5-methanesulfonamide in 2 mL of methylene chloride at 0° C. was added 0.01 mL (0.155 mmol, 1.0 equiv.) of trifluoroacetic acid. After 15 minutes the reaction was allowed to warm to room temperature. After a total of thirty minutes the reaction was poured into 15 mL of ethyl acetate and washed with 5 mL of saturated aqueous sodium bicarbonate. The organic layer was dried over anhydrous sodium sulfate, filtered and concentrated in vacuo to yield 0.0413 g (95%) of 3-(3-hydroxypropyl)-N-methyl-1H-indole-5-methanesulfonamide, homogeneous by $^1$H NMR and TLC.

EXAMPLE 6

3-(3-Hydroxypropyl)-N-N-dimethyl-1H-indole-5-methanseulfonamide

Sodium 4-nitrobenzyl sulfonate

A suspension of 100g (463 mmol, 1.0 equiv.) of 4-nitrobenzyl bromide and 64.2 g (509 mmol, 1.1 equiv.) of sodium sulfite in 500 mL of methanol and 500 mL of water was heated to reflux. The progress of the reaction was monitored by TLC. When the bromide was consumed, the reaction mixture was allowed to cool to room temperature. The product precipitated and was collected by filtration. It was thoroughly dried for sixteen hours at 65° C. at 0.05 mm Hg to give 100 g (90%) of sodium 4-nitrobenzyl sulfonate.

4-Nitrobenzyl sulfonyl chloride

To a suspension of 28.3 g (118 mmol, 1.0 equiv.) of finely ground sodium 4-nitrobenzyl sulfonate in 250 mL of toluene was added 24.6 g (118 mmol, 1.0 equiv) of finely ground phosphorous pentachloride as the solid in portions. After addition the mixture was heated to reflux for one hour. The mixture was cooled, and volatile material was removed in vacuo. The residue was dissolved in 500 mL chloroform and 250 mL of water. The organic layer was separated, dried over anhydrous sodium sulfate, filtered and concentrated to give 27.8 g (100%) of 4-nitrobenzyl sulfonyl chloride, pure by $^1$H NMR.

4-Nitro-N,N-dimethylbenzenmethanesulfonamide

Anhydrous dimethylamine was bubbled through 250 mL of cloroform at 0° C. for thirty minutes. A solution of 27.8 g (118 mmol, 1.0 equiv.) of 4-nitrobenzyl sulfonyl chloride was added dropwise at 0° C. An exothermic reaction ensued and the mixture was allowed to warm to room temperature. The mixture was concentrated in vacuo to yield 32.2 g of 4-nitro-N,N-dimethyl-benzenemethanesulfonamide contaminated with dimethylamine hydrochloride. This mixture was taken on without purification.

4-Amino-N,N-dimethylbenzenemethanesulfonamide

To a solution of 22.3 g of crude 4-nitro-N,N-dimethyl-benzenemethanesulfonamide (contaminated with dimethylamine hydrochloride as described above) in 45 mL of 2N hydrochloric acid, 100 mL of ethanol and 200 mL of water was added 5.0 g of 10% palladium on carbon. The mixture was hydrogenated in a Parr apparatus at 60 to 50 psi for three hours. The mixture was filtered and the ethanol removed in vacuo. The resulting aqueous solution was treated with 15% aqueous potassium hydroxide. Precipitate began forming at pH four. Addition of potassium hydroxide was continued until the pH had reached nine. The product was isolated by filtration and dried for sixteen hours at 65° C. at 0.05 mm Hg to give 21.0 g (83%, two steps) of 4-amino-N,N-dimethylbenzenemethanesulfonamide.

4-Hydrazinyl-N,N-dimethylbenzenemethanesulfonamide hydrochloride

To a suspension of 4.30 g (20.1 mmol, 1.0 equiv.) of 4-amino-N,N-dimethylbenzenemethanesulfonamide in 40 mL of concentrated aqueous hydrochloric acid and 20 mL of water cooled to 0° C. was added a solution of 1.38 g (20.1 mmol, 1.0 equiv.) of sodium nitrite in 20 mL of water dropwise. The reaction mixture became homogeneous during the addition. The reaction was stirred for fifteen minutes at 0° C. after the addition was complete. Meanwhile a solution of 22.6 g (100 mmol, 5.0 equiv.) of stannous chloride dihydrate in 40 mL of concentrated aqueous hydrochloric acid was prepared and cooled to −40° C. The solution of the diazonium salt was filtered into the stannous chloride solution. The reaction was allowed to warm to room temperature over the course of one hour. The reaction was then recooled to 0° C. and the precipitated product was collected by filtration. The solid was dried at 65° C. at 0.05 mm Hg for 45 minutes to yield 5.02 g (94%) of 4-hydrazinyl-N,N-dimethylbenzenemethanesulfonamide hydrochloride.

4-[2-(5-Hydroxypentylidene)hydrazinyl]-N,N-dimethylbenzenemethanesulfonamide To a solution of 5.02 g (18.9 mmol, 1.0 equiv.) of 4-hydrazinyl-N,N-dimethyl-benzenemethanesulfonamide in 20 mL of water and 20 mL of ethanol was added sufficient sodium acetate to raise the pH to four. To the resulting slurry was added 1.90 mL (20.8 mmol, 1.1 equiv.) of 3,4-dihydro-2H-pyran. The reaction was stirred for sixteen hours then diluted with 200 mL of ethyl acetate. The organic layer was washed with 10% aqueous potassium carbonate, dried over anhydrous sodium sulfate and concentrated in vacuo to yield an oil. Chromatography on silica gel using 5% methanol in methylene chloride containing 0.5% concentrated aqueous ammonium hydroxide yielded 1.67 g (28%) of pure 4-[2-(5-hydroxypentylidene)hydrazinyl]N,N-dimethylbenzenemethanesulfonamide as an oil.

3-(3-Hydroxypropyl)-N,N-dimethyl-1H-indole-5-methanesulfonamide

To a solution of 3.63 g (26.6 mmol, 5.0 equiv.) of zinc chloride in 150 mL of anhydrous 1,2-dimethoxyethane under a nitrogen atmosphere was added a solution of 1.67 g (5.33 mmol, 1.0 equiv.) of 4-[2-(5-hydroxypentylidene)hydrazinyl]-N,N-dimethylbenzenemethanesulfonamide in 50 mL of anhydrous 1,2-dimethoxyethane. The solution was heated to reflux for sixteen hours. The reaction was cooled to room temperature and the volume concentrated to 25 mL in vacuo. The residue was diluted with 100 mL of ethyl acetate and washed with 20 mL portions of water and saturated aqueous sodium chloride. The organic layer was dried over anhydrous sodium sulfate, filtered and concentrated in vacuo to yield an oil. The oil was purified by chromatography on silica gel using 5% methanol in methylene chloride containing 0.5% concentrated aqueous ammonium hydroxide to obtain 0.409 g (26%) of 3-(3-hydroxypropyl)-N,N-dimethyl-1H-indole-5-methanesulfonamide.

Compounds of type:

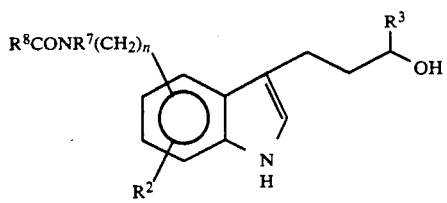

VI and

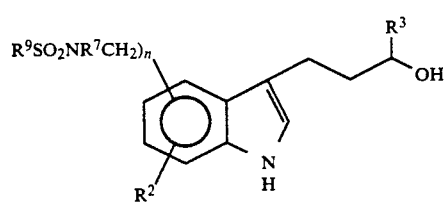

VI

EXAMPLE 7
N-[[3-(3-Hydroxypropyl)-1H-indol-5-yl]methyl]methanesulfonamide

N-[(4-Nitrophenyl)methyl]methanesulfonamide

To a solution of 25.0 g (133 mmol, 1.0 equiv.) of 4-nitro benzylamine hydrochloride in 500 mL of methylene chloride at 0° C. was added 46.4 mL (331 mmol, 2.5 equiv.) of triethylamine followed by 11.3 mL (146 mmol, 1.1 equiv.) of methanesulfonyl chloride dropwise. The reaction was stirred for thirty minutes at 0° C. then diluted with 500 mL of chloroform. The organic layer was washed with 150 mL portions of 1N HCl and saturated sodium chloride. The organic layer was dried over magnesium sulfate, filtered and concentrated to give 25.8 g (85%) of N-[(4-nitrophenyl)methyl]methanesulfonamide.

N-[(4-Aminophenyl)methyl]methanesulfonamide

To a suspension of 25.9 g (113 mmol, 1.0 equiv.) or N-[(4-nirropnenyl)mernyl]methanesulfonamide in 113 mL of 1N HCl (113 mmol, 1.0 equiv.), 113 mL of water and 225 mL of ethanol was added 5.18 g of 10% palladium on carbon. This mixture was hydrogenated in a Parr apparatus at 60 psi for sixteen hours. The mixture was filtered through Celite. The ethanol was removed in vacuo and the pH adjusted to 9, at which point the product had precipitated. The precipitate was isolated by filtration and dried in vacuo to yield 18.0 g (80%) of N-[(4-aminophenyl)methyl]methanesulfonamide.

N-[(4-Hydrazinylphenyl)methyl]methanesulfonamide hydrochloride

To a suspension of 18.0 g (89.9 mmol, 1.0 equiv.) of N-[(4-aminophenyl)methyl]methanesulfonamide in 85 ml of water and 175 mL of concentrated aqueous hydrochloric acid at 0° C. was added a solution of 6.21 g (89.9 mmol, 1.0 equiv.) of sodium nitrite in 85 mL of water. The reaction mixture was stirred for fifteen minutes. Meanwhile a solution of 101.6 g of stannous chloride dihydrate in 175 mL of concentrated aqueous hydrochloric acid was prepared and cooled to −55° C. The solution of the diazonium salt was filtered into the stannous chloride solution. The reaction was maintained between −55° C. and −35° C. for one hour. The crystalline material was collected by filtration and dried under high vacuum at 65° C. for 16 hours to yield 23.9 g (>100%) of crude N-[(4-hydrazinylphenyl)methyl]methanesulfonamide hydrochloride.

N-[[4-[2-(5-Hydroxypentylidene)hydrazinyl]phenyl]methyl]methanesulfonamide

To a solution of 23.9 g of crude N-[(4-hydrazinylphenyl)methyl]methanesulfonamide hydrochloride in 175 mL of water and 300 mL of ethanol was added sufficient sodium acetate to bring the pH to 4. To the resulting suspension was added 10.4 mL (114 mmol, 1.3 equiv.) of 3,4- dihydro-2H-pyran. The mixture was then stirred for twenty hours at room temperature. The ethanol was removed in vacuo. The pH was raised to 10 by adding solid potassium carbonate and the mixture was extracted three times with 50 mL portions of methylene chloride. The combined organic layers were washed with 25 mL of saturated aqueous sodium chloride, dried over magnesium sulfate and filtered to give an oil. The oil was purified by chromatography on silica gel using 5% methanol in methylene chloride containing 0.5% concentrated aqueous ammonium hydroxide to yield 11.1 g (39%, two steps) of pure N-[[4-[2-(5-hydroxypentylidene)hydrazinyl]phenyl]methyl]methanesulfonamide.

N-[[3-(3-Hydroxypropyl)-1H-indol-5-yl]methyl]methanesulfonamide

To a solution of 25.2 g (185 mmol, 5.0 equiv.) of zinc chloride in 900 mL of anhydrous 1,2-dimethoxyethane under nitrogen was added a solution of 11.1 g (37.0 mmol, 1.0 mmol) of N-[[4-[2-(5-hydroxypentylidene)hydrazinyl]phenyl]methyl]methanesulfonamide. The solution was refluxed for forty-eight hours then cooled to room temperature. The reaction mixture was filtered and concentrated in vacuo. The residue was dissolved in 500 mL of ethyl acetate and washed with 100 mL portions of water and saturated aqueous sodium chloride. The organic layer was dried over magnesium sulfate, filtered and concentrated in vacuo to yield 11.0 g of an oil. This was purified by chromatography on silica gel using gradient elution from 5% methanol in methylene chloride containing 0.5% concentrated aqueous ammonium hydroxide to 10% methanol in methylene chloride containing 1% concentrated aqueous ammonium hydroxide to yield 6.97 g (67%) of pure N-[[3-(3-hydroxypropyl)-1H-indol-5-yl]methyl]methanesulfonamide.

Substitution of an acyl halide for the alkylsulfonyl chloride in step 1 of the above sequence provide the acyl analog of the sulfonyl product.

Compounds of type:

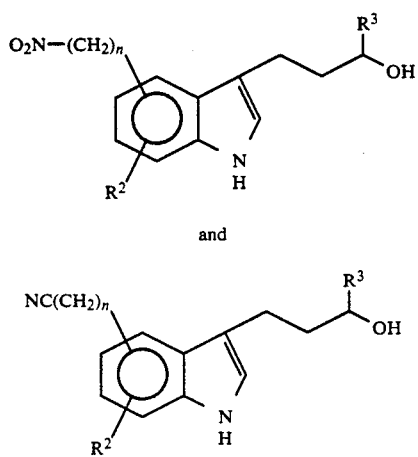

and

EXAMPLE 8

(5-Cyano-1H-indol-3-yl)propanol

5-Cyano-3-(dimethylamino))methyl-1H-indole

To a solution of 14.0 g (98.5 mmol, 1.0 equiv.) of 5-cyanoindole in 35 mL of ethanol was added 8.7 mL (108 mmol, 1.1 equiv.) of 40% aqueous formaldehyde and 12.2 mL (108 mmol, 1.1 equiv) of 40% aqueous dimethylamine. The flask was fitted with a reflux condenser topped with a cold finger condenser at −78° C. The solution was heated to reflux for eight hours at which time TLC indicated absence of starting material. The solution was poured into 350 mL of chloroform and washed once with 50 mL of 10% aqueous sodium carbonate. The organic layer was separated, dried over anhydrous sodium sulfate, filtered and concentrated to yield 19.6 g (100%) of 5-cyano-3-(dimethylamino)methyl-1H-indole, pure by $^1$H NMR analysis.

N,N,N-trimethyl-1-(5-cyano-1H-indol-3-yl)methanaminium iodide

To a solution of 2.7 g (13.6 mmol, 1.0 equiv.) of 5-cyano-3-(dimethylamino)methyl-1H-indole in 125 mL of THF at 0° C. was added 1.3 mL (20.3 mmol, 1.5 equiv.) of methyl iodide dropwise. After five minutes the solution was allowed to warm to room temperature and stirred for one hour. The resulting precipitate was filtered and dried in vacuo to yield 4.4 g (96%) of N,N,N-trimethyl-1-(5-cyano-1H-indol-3-yl)methanaminium iodide, pure by $^1$H NMR analysis.

Methyl 2-methoxycarbonyl-3-(5-cyano-1H-indol-3-yl)propanoate

To a solution of 21.5 g (63.0 mmol, 1.0 equiv.) of N,N,N-trimethyl-1-(5-cyano-1H-indol-3-yl)methanaminium iodide in 300 mL of methanol was added 14.6 g (94.5 mmol, 1.5 equiv.) of sodiodimethylmalonate. The mixture was warmed to reflux for sixteen hours. The solution was cooled to room temperature and diluted with 1000 mL of chloroform. The organic layer was washed once with 250 mL of saturated aqueous sodium bicarbonate solution. The organic layer was separated, dried over anhydrous sodium sulfate, filtered and concentrated. The resulting residue was filtered through a plug of silica gel with 1:1 ethyl acetate:hexane to remove unreacted dimethyl malonate. This provided 18.95 g (100%) of methyl 2-methoxycarbonyl-3-(5-cyano-1H-indol-3-yl)propanoate Methyl 3-(5-cyano-1H-indol-3-yl)propanoate.

To a solution of 1.14 g (3.98 mmol, 1.0 equiv.) of methyl 2-methoxycarbonyl-3-(5-cyano-1H-indol-3-yl)propanoate in 20 mL of pyridine was added 1.19 g (7.96 mmol, 2.0 equiv.) of sodium iodide. The mixture was heated to reflux for sixteen hours. The solution was cooled and diluted with 150 mL of chloroform. The organic layer was washed once with 25 mL of saturated aqueous sodium bicarbonate solution. The organic layer was separated, dried over anhydrous sodium sulfate, filtered and concentrated. The resulting residue was filtered through a plug of silica gel with 1:1 ethyl acetate:hexane to remove colored impurities to provide 0.734 g (81%) of methyl 3-(5-cyano-1H-indol-3-yl)propanoate.

(5-Cyano-1H-indol-3-yl)propanol

To a suspension of 0.184 g (4.86 mmol, 2.0 equiv.) of lithium aluminum hydride in 10 mL of THF at 0° C. was added a solution of 0.555 g of methyl 3-(5-cyano-1H-indol-3-yl) propanoate dropwise. The resulting suspension was stirred at 0° C. for thirty minutes then quenched with 0.18 mL of water, 0.18 mL of 15% aqueous sodium hydroxide and 0.54 mL of water. The resulting suspension was filtered through Celite. The solution was concentrated and the residue filtered through a plug of silica gel with 1:1 ethyl acetate:hexane to yield 0.470 g (97%) of (5-cyano-1H-indol-3-yl)propanol.

EXAMPLE 9

5-Nitro-3-(3-hydroxypropyl)indole 5-(5-Nitroindol-3-ylmethyl)-2,2-dimethyl-1,3-dioxane-4,6-dione An adaption of the procedure of Flaugh was used. Thus, a solution of 5-nitroindole (50.0 g, 0.31 mol), Meldrum's acid (46.0 g, 0.32 mol), 37% aqueous formaldehyde (26.0 mL, 0.32 mol) and proline (1.8 g, 0.016 mol) in 200 mL of acetonitrile was stirred at room temperature for 18 h. The resulting thick yellow slurry was filtered and the filtercake was washed with acetonitrile, then acetone and finally with ether. This material was dried in vacuo to give the title compound (80.0 g, 81%) as a bright yellow solid, m.p. 182° C. (dec). The mother liquor was concentrated and then diluted with H$_2$O, and the resulting solid was collected and washed and dried as before. This gave a second crop of the product (7.0 g) as a darker yellow solid. Total yield =87.0 g (89%).

Ethyl 5-nitro-3-indolepropionate

To a solution of 5-(5-nitroindol-3-ylmethyl)-2,2-dimethyl-1,3-dioxane-4,6-dione (10.0 g, 0.031 mol) in a mixture of pyridine (80 mL) and absolute ethanol (20 mL) was added 0.1 g of copper powder and the mixture was refluxed under Ar for 2h. After being stirred at room temperature for 66 h the mixture was refluxed for an additional 1 h. The cooled mixture was filtered and the filtrate was evaporated. The resulting residue was triturated with ether and a little $CH_2Cl_2$ to give the title compound (7.3 g, 89%) as a solid, m.p. 118°–121° C.

5-Nitro-3-(3-hydroxypropyl)indole

To a suspension of 95% $LiAlH_4$ (2.20 g, 0.058 mol) in 60 mL of dry THF was added a solution of ethyl 5-nitro-3-indolepropionate (7.30 g, 0.028 g mol) in 100 mL of dry THF, at 0° C. under Ar. After stirring for 20 min the mixture was quenched by cautiously adding 3 mL of $H_2O$. The resulting suspension was stirred for 10 min and then it was filtered and the filtercake was washed with additional THF. The filtrate was evaporated and the residue was taken up in ether, dried ($Na_2SO_4$) and evaporated, and the resulting solid was triturated with hexane to give the title compound (4.30 g, 70%) as a yellow solid, m.p. 107°–110° C.

EXAMPLE 10

1-[5-Acetyl-1H-indol-3-yl]-3-propanol

4-Amino-3-iodoacetophenone

To a solution containing 4-aminoacetophenone (4.05 g, 30 mmol) in glacial acetic acid (60 mL) and water (10 mL) was added dropwise a solution of iodine monochloride (4.97 g, 31 mmol) in acetic acid (15 mL). After the addition was complete, the reaction was heated at 90° C. for five min. then cooled to 23° C. and allowed to stand for one h. The excess ICl was discharged by the addition of saturated sodium bisulfite (15 mL). The solvent was removed in vacuo and the residue dissolved in $CH_2Cl_2$, washed with saturated NaCl and finally with water. The organic phase was dried with $Na_2SO_4$, filtered, and concentrated in vacuo. Silica gel chromatography (Hexane:ethyl acetate gradient; 10–50% EtOAc) afforded 4-amino-3-iodoacetophenone (6.15 g, 82.3%).

5-Acetyl-3-[3-(t-butyldimethylsiloxy)propyl]-2-trimethylsilyl-1H-indole

To a solution of 4-amino-3-iodoacetophenone (6.15 g, 25 mmol) in 1,2-dimethoxyethane (250 mL) was added saturated $Na_2CO_3$ (20 mL), 1-trimethylsilyl-5-t-butyl-dimethylsiloxypent-1-yne (13.36 g, 49 mmol), and $Pd(PPh_3)_4$ (2.85 g, 2 mmol). After heating the mixture at reflux for 48 h the solvent was removed in vacuo. The residue was dissolved in ethyl acetate and washed with saturated NaCl and next with water. The organic phase was dried over $MgSO_4$, filtered, and concentrated in vacuo. Silica gel chromatography (Hexane:ethyl acetate gradient; 10–50% EtOAc) and crystallization from $CH_2Cl_2$:hexanes afforded 5-acetyl-3-[3-(t-butyldimethylsiloxy)propyl]-2-trimethylsilyl-1H-indole (5.76 g, 58%).

1-[5-Acetyl-1H-indol-3-yl]-3-propanol

To a solution of 5-acetyl-3-[3-(t-butyldimethylsiloxy)propyl]-2-trimethylsily 1-1H-indole (1.8 g, 5 mmol) in acetonitrile (100 mL) was added a 50% HF solution (4 mL). After stirring for 24 h at 23° C., the reaction was made basic (pH 10) by the addition of 50% NaOH solution and concentrated in vacuo. The residue was dissolved in ethyl acetate and washed with saturated NaCl and next with water. The organic phase was dried over $MgSO_4$, filtered, and concentrated in vacuo. Silica gel chromatography ($CH_2Cl_2$:MeOH:$NH_4OH$; 95:5:0.5) of the concentrate afforded 1-[5-acetyl-1H-indol-b 3-yl]-3-propanol (0.91 g, 94%).

EXAMPLE 11

5-Fluoro-3-(3-hydroxypropyl)indole

5-Fluoroindole-3-propionic acid

A modification of a procedure reported by Johnson (H. E. Johnson and D. G. Crosby, *J. Org. Chem.*, 25, 569 (1969)) for the preparation of indole-3-propionic acid was used.

Thus, a solution of 5-fluoroindole (1.35 g, 0.010 mol) in 10 mL of acetic acid containing acrylic acid (1.5 mL, 0.022 mol) and acetic anhydride (1.9 mL, 0.02 mol) was heated (oil bath) at 90° C. under Ar for 5 days. The volatiles were then removed in vacuo and the residue was taken up in 3N NaOH. Insoluble material was removed by filtration and the filtrate was acidified with conc. HCl and then extracted with $CH_2Cl_2$. The organic extract was dried ($Na_2SO_4$) and evaporated to give the product (1.191 g, 57%) as a solid which was used without further purification: IR (neat) 3420, 1710 $cm^{-1}$; $^1$Hnmr (200 MHz, $CDCl_3$) δ7.94 (br s, 1H), 7.28–7.18 (m, 3H), 7.05 (d, J=2.5 Hz, 1H), 6.93 (dt, J=9.0, 2.6 Hz, 1H), 3.05 (t, J=7.5 Hz, 2H), 2.73 (t, J=7.6 Hz, 2H).

By appropriate modification of the general method, other Formula II compounds are readily obtainable.

5-Fluoro-3-(3-hydroxypropyl)indole

To a suspension of $LiAlH_4$ (433 mg, 11.4 mmol) in 20 mL of dry tetrahydrofuran at 5°–10° C. under Ar was added a solution of 5-fluoroindole-3-propionic acid (1.179 g, 5.7 mmol) in 5 mL of tetrahydrofuran. After 10 min the cooling bath was removed and the mixture was stirred at room temperature for 30 min and finally it was heated to reflux for 30 min. The resulting gummy mixture was allowed to cool to room temperature and then the reaction was quenched by the sequential addition of 0.5 mL of $H_2O$, 0.5 mL of 15% NaOH solution and finally 1.5 mL of $H_2O$. The mixture was then diluted with ethyl acetate, dried ($MgSO_4$) and evaporated to give a yellow-green oil. Flash chromatography ($SiO_2$/$CH_2Cl_2$-ethyl acetate=2:1) afforded the product (918 mg, 83%) as an oil: IR (neat) 3420, 1583 $cm^{-1}$; $^1$Hnmr (200 MHz, $CDCl_3$) δ7.94 (br s, 1H), 7.28–7.20 (m, 2H), 7.03 (d, J=2.4 Hz, 1H), 6.92 (dt, J=9.1, 2.5 Hz, 1H), 3.71 (t, J=6.4 Hz, 2H), 2.80 (t, J=7.5 Hz, 2H), 2.02–1.88 (m, 2H), 1.33 (br s, 1H).

EXAMPLE 12

Ethyl 3-[3-hydroxyprop-1-1H-indole-5-carboxylate

Ethyl 3-[3-[[(1,1-dimethylethyl)dimethylsilyl]oxy]prop-1-yl]-2-trimethylsilyl-1H-indole-5-carboxylate A mixture of ethyl 4-amino-3-iodobenzoate {Hirschfeld et al. *J. Med Chem.* 1992, 35, 2231–2238.} (7.80 g, 26.8 mmol), [5-[[(1,1-dimethylethyl)dimethylsilyl]oxy]-1-pentynyl]tri methylsilane (9.41 g, 34.8 mmol), tetra-n-butylammonium chloride (7.44 g, 26.8 mmol), sodium carbonate (14.20 g, .134 mol), triphenylphosphine (0.35 g, 1.3 mmol), and palladium (II) acetate (0.30 g, 1.3 mmol) in 200 mL of DMF, was heated at 98° C. under $N_2$ for 2 h. The solution was cooled, and the bulk of the DMF was removed in vacuo. The mixture was diluted with ethyl acetate, and the organic solution was washed with aqueous NaHCO₃, dried (brine, MgSO₄), filtered, and concentrated in vacuo. Silica gel chromatography (10:1 hexanes-EtOAc) of the concentrate yielded the title compound (7.49 g, 65%) as a crystalline solid. Recrystallization from hexanes provided an analytical sample as a white crystalline solid: mp 115°–116° C. Anal. Calcd for $C_{23}H_{39}N_1O_3Si_2$: C 63.69; H, 9.06; N, 3.23. Found: C, 63.54; H, 9.11; N, 3.17.

Ethyl 3-[3-hydroxy-prop-1-yl]-1H-indole-5-carboxylate

A solution of ethyl 3-[3-[(1,1-dimethylethyl)dimethylsilyloxy]prop-1-yl]-2-trimethylsilyl-1H-indole-5-carboxylate (5.0 g, 11.5 mmol), and aqueous 48% HF (1.9 g, 46.0 mmol) in 140 mL of MeCN was stirred at 23° C. for 3.5 h. The solution was quenched with 10% Na₂CO₃, and the organic material was extracted into ethyl acetate. The organic solution was dried (brine, MgSO₄), filtered, and concentrated in vacuo. Silica gel chromatography (50–100% EtOAc-hexanes gradient) of the concentrate yielded the title compound (2.79 g, 98%) as a white crystalline solid: mp 111°–112° C. Anal. Calcd for $C_{14}H_{17}N_1O_3$: C, 68.00; H, 6.93; N, 5.66. Found: C, 67.94; H, 6.78; N, 5.65.

EXAMPLE 13

3-(3-Hydroxydroyl)-1H-indole-5-carboxylic acid

To a solution of methyl 3-(3-hydroxypropyl)-1H-indole-5-carboxylate (5.0 g, 21.46mmol) in 50 mL ethanol was added 30 mL of 15% potassium hydroxide in ethanol. The mixture was heated to reflux for 1 h. The mixture was cooled to 0° C. and acidified with concentrated hydrochloric acid to pH 6. The ethanol was removed in vacuo. The residue was diluted with 250 mL of ethyl acetate and washed with 50 mL of water. The organic layer was dried over anhydrous sodium sulfate, filtered and concentrated in vacuo to yield 3-(3-hydroxypropyl)-1H-indole-5-carboxylic acid (4.30 g, 92%).

EXAMPLE 14

3-(3-Hydroxypropyl)-N-(phenylmethyl)-1H-indole-5-carboxamide

To a mixture of 3-(3-hydroxypropyl)-1H-indole-5-carboxylic acid (4.30 g, 19.63 mmol), triethylamine (3.97 g, 39.26 mmol) and benzylamine (2.10 g, 19.63 mmol) in 150 mL acetonitrile was added 2-chloro-1-methylpyridinium iodide (6.04 g, 23.68 mmol). The mixture was heated to reflux for 16 h. The solution was cooled to room temperature, 70 mL of 0.5N hydrochloric acid added, and the acetonitrile removed in vacuo. The residue was extracted with 250 mL of ethyl acetate. The organic layer was separated and the aqueous layer reextracted with three 50 mL portions of ethyl acetate. The combined organic layers were dried over anhydrous sodium sulfate, filtered and concentrated in vacuo. Silica gel chromatography (95:5:0.5 CH₂Cl₂-MeOH-NH₄OH) of the concentrate yielded 3-(3-hydroxypropyl)-N-(phenylmethyl)-1H-indole-5-carboxamide (2.26 g, 37%).

Compounds of Formula V

The conversion of Formula VI compounds to compounds of Formula V is accomplished by standard synthetic reactions in which an alkanol moiety is converted to an alkyl-[leaving group] moiety. The following examples are intended to be demonstrative but not limiting.

EXAMPLE 5

3-(5-Ethanesulfonylamino-1H-indol-3-yl)propyl methanesulfonate.

To a solution of 3-(5-ethanesulfonylamino-1H-indol-3-yl)propanol (0.59 g, 2.1 mmol) in 20 mL of THF at 0° C. was added triethylamine (0.58 mL, 4.2 mmol) followed by the dropwise addition of methanesulfonyl chloride (0.24 mL, 3.1 mmol). The reaction was stirred for 30 minutes at 0° C. The reaction was poured into a mixture of saturated NaHCO₃ and ethyl acetate. The organic phase was separated and the aqueous phase reextracted with three portions of ethyl acetate. The combined organic layers were washed with a saturated NaCl solution, dried over anhydrous K₂CO₃, filtered, and concentrated in vacuo to yield 3-(5-ethanesulfonylamino-1H-indol-3-yl)propyl methanesulfonate (0.75 g, >99%) which was used without further purification.

EXAMPLE 16

3-[5-[(Phenylmethoxycarbonyl)amine]-1H-indol-3-yl]propyl-4-methylbenzenesulfonate To a solution of alcohol (0.31 g, 0.96 mmol), triethylamine (0.15 g, 1.4 mmol), and 4-dimethylaminopyridine (DMAP) (0.01 g) in CH₂Cl₂ (10 mL) at 0° C. was added TsCl (0.27 g, 0.96 mmol). The reaction was allowed to warm to 23° C. and stand 16 h. At the end of this time, additional TsCl (0.068 g) and triethylamine (0.038 g) were added and allowed to react for 3 h. The reaction was treated with ice/water and the organic phase was separated, extracted with saturated NaCl solution, dried with K₂CO₃, filtered, and concentrated in vacuo. Silica gel chromatography (70:30 hexane:ethyl acetate) of the concentrate afforded 3-[5-[(phenylmethoxycarbonyl)amine]-1H-indol-3-yl]propyl 4-methylbenzenesulfonate (0.39 g, 85%) whose structure was confirmed by NMR and MS analysis.

EXAMPLE 17

3-[5-[[(Methylamino)sulfonyl]methyl]-1H-indol-3-yl]-propylmethanesulfonate

To a solution of 5.16 g (18.3 mmol, 1.0 equiv.) of 3-(3-hydroxypropyl)-N-methyl-1H-indole-5-methanesulfonamide and 3.84 mL (27.4 mmol, 1.5 equiv.) of triethylamine in 100 mL of anhydrous acetonitrile and 100 mL of methylene chloride at 0° C. was added 1.77 mL (22.8 mmol, 1.25 equiv.) of methanesulfonyl chloride dropwise. The reaction was stirred for thirty minutes at 0°C. then diluted with 250 mL of ethyl acetate. The organic layer was washed with 50 mL portions of saturated aqueous sodium bicarbonate and saturated aqueous sodium chloride. The organic layer was dried over anhydrous magnesium sulfate, filtered and concentrated in vacuo to yield an oil which was used directly in the next step.

EXAMPLE 18

5-Nitro-3-(3-bromopropyl)indole

To a solution of triphenylphosphine (6.70 g, 0.025 mol) in 80 mL of acetonitrile was added a solution of 5-nitro-3-(3-hydroxypropyl)indole (4.30 g, 0.020 mol) in 75 mL of acetonitrile, followed by a solution of CBr₄ (9.00 g, 0.027 mol) in 25 mL of acetonitrile, at 0° C. under Ar. The mixture was stirred at room temperature for 3 h and then it was evaporated and the residue was chromatographed (SiO₂/EtOAc-hexane, 1;9 then 1:4) to give the title compound (4.60 g, 84%) as a solid, m.p. 92°-95° C.

EXAMPLE 19

5-Fluoro-3-(-p-toluenesulfonyloxypropyl)indole

To a solution of 5-fluoro-3-(3-hydroxypropyl)indole (917 mg, 4.75 mmol) in 20 mL of $CH_2Cl_2$ at 0° C. under Ar was added triethylamine (728 μL, 5.23 mmol), followed by a solution of p-toluenesulfonyl chloride (994 mg, 5.23 mmol) in 5 mL of $CH_2Cl_2$ and then a catalytic amount of 4-dimethylaminopyridine (59 mg, 0.48 mmol). The reaction mixture was stirred at 0° C. for 30 min and then at room temperature for 1½h. Evaporation of the mixture followed by chromatography (SiO₂/$CH_2Cl_2$) of the residue gave a gum. The gum was dissolved in ether and then the solution was diluted with hexane until an oil separated. Addition of a small amount of $CH_2Cl_2$ led to dissolution of the oil and crystallization of the product. Storage at −20° C. and then filtration and drying of the residue in vacuo gave the product (1.378 g, 84%) as fluffy white needles m.p. 99° C.; IR ($CH_2Cl_2$) 3470, 1360, 1178 cm$^{-1}$; ¹Hnmr (200 MHz, CDCl₃) δ7.90 (br s, 1H), 7.61 (d, J=8.4 Hz, 2H), 7.30 (d, J=8.4 Hz, 2H), 7.27-7.20 (m, 1H) 7.08 (dd J=9.6 2.6 Hz, 1H) 6.96-6.94 (m, 1H), 6.88 (dd, J=9.0, 2.5 Hz, 1H), 4.06 (t, J=6.2 Hz, 2H), 2.74 (t, J=7.2 Hz, 2H), 2.42 (s, 3H), 1.99 (dq, J=7.2, 6.2 Hz, 2H).

EXAMPLE 20

Ethyl 3-[3-iodopropy-1-yl]-1H-indole-5-carboxylate

A mixture of ethyl 3-[3-hydroxy-prop-1-yl]-1H-inodole-5-carboxylate (2.64 g, 10.7 mmol), triethylamine (1.52 g, 15 mmol), and methanesulfonyl chloride (1.83 g, 16 mmol) in 50 mL of acetonitrile was stirred at 0° C. for 1 h. The acetonitrile was removed in vacuo and the organic material was diluted with ethyl acetate. The organic solution was washed with aqueous $Na_2CO_3$, dried (brine, $MgSO_4$), filtered, and concentrated in vacuo. The concentrate was dissolved in 100 mL of acetonitrile and powdered KI (3.55 g, 21.4 mmol) added. The solution was heated at reflux for 1.5 h, then cooled, poured into water and extracted into EtOAc. The combined organic extracts were dried (brine, $MgSO_4$), filtered, and concentrated in vacuo. Silica gel chromatography (5:1 hexanes-EtOAc) of the concentrate yielded the title compound (3.50 g, 92%) as a white crystalline solid: mp 81° C. Anal. Calcd for $C_{14}H_{16}I_1N_1O_2$: C, 47.08; H, 4.51; N, 3.92. Found: C, 47.12; H, 4.44; N, 3.89.

Compounds of Formula III

EXAMPLE 21

1-(5-Methoxy-4-pyrimidinyl)piperazine—Method 1

To a solution of piperazine (38.40 g, 0.45 mole) in $CH_3CN$ (225 mL) was added dropwise a $CH_3CN$ (100 mL) solution containing 4-chloro-5-methoxypyrimidine (6.45 g, 0.04 mole) while under nitrogen atmosphere. After the addition was complete the reaction was heated at 60° C. for 0.75 h. The reaction was concentrated under reduced pressure and the residue dissolved in $CH_2Cl_2$ and extracted with 5% $NaHCO_3$ and $H_2O$. The organic phase was dried with $K_2CO_3$, filtered, and concentrated under reduced pressure. Silica gel chromatography ($CH_2Cl_2$: MeOH:NH₄OH; 92:8:0.8) of the concentrate afforded II (7.63 g, 88.1%). Treatment of the base (1.0 g) with ethanolic HCl and crystallization from EtOH/i-PrOH yielded the hydrochloride salt of II (0.50 g, 39.1%, m.p. 207°-211°).

1-(5-Methoxy-4-pyrimidinyl)piperazine—Method 2

4,6-Dihydroxy-5-methoxypyrimidine

A modified procedure of Bretschneider, Richter, and Klötzer, Monatsh. Chem. 96(6), 1661-76 (1965), was used. Absolute methanol (1.0 L) was added with ice bath cooling to sodium methoxide (175 g, 3.24 moles) in a 3 L round bottom flask. When the mixture had cooled to less than 20° C., dimethyl methoxymalonate (162.14 g, 1.00 mole) was added, and then solid formamidine acetate (104.11 g, 1.00 mole) was added. The mixture was stirred i the ice bath for 30 minutes, and then refluxed for 1 hour. The mixture was cooled in a cold water bath and then concentrated HCl (about 350 mL) was added until the mixture was strongly acidic on pH test paper. The precipitate was filtered, suspended in cold water (about 400 mL), and then filtered again. The white powder was dried in vacuo (125.84 g, 88.7%), and carried on without further purification.

4,6-Dichloro-5-methoxypyrimidine

A modified procedure of Bretschneider, Richter, and Klötze, Monatsh. Chem. 96(6), 1661-76 (1965), was used. A mixture of 4,6-dihydroxy-5-methoxy-pyrimidine (125.84 g, 0.887 mole), POCl₃ (700 mL), and N,N-diethylaniline (50 mL) was refluxed for 3 hours to give a brown solution. The solution was cooled and then the excess POCl₃ was removed in vacuo. Hexane (about 300 mL) was added to the residue and the mixture was refluxed with stirring. The hot hexane layer was decanted into a beaker, and residue treated two more times with hot hexane. The hexane extracts (total volume about 1 L) were concentrated in vacuo to give the crude product as a white solid (116.5 g, 73.3%). This material was recrystallized from pet ether to give colorless needles (92.0 g +16.51 g second crop, 93.1% total recovery).

4-Chloro-5-methoxy-4-(1-piperazinyl)pyrimidine

Piperazine (30 g) was dissolved in water (150 mL) and then solid 4,6-Dichloro-5-methoxypyrimidine (10.00 g, 55.8 mmole) was added. The mixture was vigorously stirred for 2 h at room temperature during which the 4,6-dichloro-5-methoxypyrimidine dissolved. The product was extracted from the aqueous reaction mixture with methylene chloride (yield 12.67 g, 99.2%). A sample (5 g) of the crude product was chromatographed on silica gel using a gradient of 20–40% methanol/ethyl acetate as the eluent. The product was then dissolved in acetonitrile and concentrated HCl added to give the salt as a white powder which was dried in vacuo to give the analytical sample (4.0 g, m.p.: 169°-173° C. bubbles).

Anal. Calcd for $C_9H_{13}N_4OCl\cdot1.5$ HCl·0.2 $H_2O$, C, 37.67; H, 5.24; N, 19.53 $H_2O$; 1.26.
Found: C, 37.63; H, 4.99; N, 1946 $H_2O$; 1.47.

1-(5-Methoxy-4-pyrimidinyl)piperazine

Piperazine (20 g) was dissolved in water (100 mL) in a Parr bottle and then solid 4,6-dichloro-5-methoxypyrimidine (5.00 g, 27.9 mmole) was added. The mixture was vigorously stirred for 2 h at room temperature during which the 4,6-dichloro-5-methoxypyrimidine dissolved. The stirring bar was removed, catalyst (10% Pd/C, 1.0 g) was added to the turbid solution, and the mixture was then hydrogenated (60 psi, 3 h) at room temperature. The catalyst was filtered off and the filtrate extracted 3 times with $CH_2Cl_2$. The $CH_2Cl_2$ extracts were dried over $Na_2SO_4$ and concentrated in vacuo to give a clear oil which solidified upon standing (3.34 g, 61.7%). This crude product was Kügelrohr distilled (yield 3.24 g), dissolved in acetonitrile, and concentrated HCl was added to precipitate the product as a white powder which was dried in vacuo (4.32 g, 94.0% from crude product, m.p. 219°–221.5° C.).

EXAMPLE 22

1-(5-Methoxy-4-pyrimidinyl)-2-methylpiperazine

Method 1

1-(t-Butoxycarbonyl)-3-methylpiperazine

To a cold (−5° C.) solution of 2-methylpiperazine (5.00 g, 0.05 mole) in 200 mL of $CH_2Cl_2$ under Ar was added a solution of di-t-butyl dicarbonate (10.9 g, 0.05 mole) in 100 mL of $CH_2Cl_2$ over 1 h. The resulting mixture was stirred at −5° C. for 1 h and then at r.t. for 2 h. The solution was then washed ($H_2O$), dried ($Na_2SO_4$) and evaporated to give an oil which was chromatographed ($SiO_2$/ethyl acetate then ethyl acetate-MeOH-$NH_4OH$ 10:1:0.1) to give the product (4.30 g, 43%) as an oil. This material was used without further purification: $^1H$ nmr (200 MHz, $CDCl_3$) δ4.15–3.75 (br s, 2H), 3.0–2.6 (m, 4H), 2.47–2.35 (m, 1H), 1.48 (s, 9H), 1.08 (d, J=6.7 Hz, 3H).

1-(t-Butoxycarbonyl)-4-(5-methoxy-4-pyrimidyl)-3-methylpiperazine

A mixture of 1-(t-butoxycarbonyl)-3-methylpiperazine (2.0 g, 0.01 mole), 4-chloro-5-methoxypyrimidine (1.5 g, 0.01 mole) and diisopropylethylamine (2.6 mL, 0.015 mole) in 25 mL of dry acetonitrile was heated to reflux under Ar for 60 h. The resulting solution was diluted with ether and then washed ($H_2O$, brine), dried ($Na_2SO_4$) and evaporated to give a gum. This gum was triturated with hexane (×3) and the supernatant was evaporated to give a gum. Flash chromatography ($SiO_2$/ethyl acetate-hexane=1:1, then ethyl acetate) of this material gave first 4-chloro-5-methoxypyrimidine (0.4 g, 27%) and then the desired product (1.2 g, 30%) as a light pink solid: m.p. 70°–72° C.; IR (KBr) 1690, 1575 $cm^{-1}$; $^1H$ nmr (200 MHz, $CDCl_3$)δ8.33 (s, 1H), 7.90 (s, 1H), 4.79 (br s, 1H), 4.4–3.8 (m, 3H), 3.86 (s, 3H), 3.35–2.90 (m, 3H), 1.48 (s, 9H), 1.21 (d, J=6.7 Hz, 3H).

1-(5-Methoxy-4-pyrimidinyl)-2-methylpiperazine

A solution of 1-(t-butoxycarbonyl)-4-(5-methoxy-4-pyrimidinyl)-3-methylpiperazine (1.70 g, 4.2 mmol) and trifluoroacetic acid (5 mL) in 50 mL of $CH_2Cl_2$ was stirred at r.t. under Ar for 18 h. The solution was evaporated, the residue was taken up in water and the mixture was basified (pH8) with 15% aqueous NaOH. The resulting (pH 8) mixture was extracted with ethyl acetate and the organic phase was washed ($H_2O$, brine), dried ($Na_2SO_4$) and evaporated to give a semi-solid. This material was taken up in ether, filtered to remove insoluble material and the solution was evaporated to give the product (0.80 g, 92%) as an oil. It was used without further purification: IR (neat) 3300, 1580, 1540 $cm^{-1}$; $^1H$ nmr (200 MHz, $CDCl_3$) δ8.32 (s, 1H), 7.87 (s, 1H), 4.83–4.68 (m, 1H), 4.26–4.19 (m, 1H), 3.85 (s, 3H), 3.26–3.17 (m, 1H), 3.12–3.01 (m, 2H), 2.94–2.80 (m, 2H), 1.29 (d, J=6.8 Hz, 3H).

4-(5-Methoxy-4-pyrimidinyl)-2-methylpiperazine

Method 2

A solution of 2-methylpiperazine (20 g) in water (100 mL) was reacted with solid 4,6-dichloro-5-methoxypyrimidine (5.00 g, 27.9 mmole) in a procedure similar to that given for Method 2 of Example 14. After hydrogenation and filtration of the catalyst, the product was extracted from the filtrate with $CH_2Cl_2$. The extracts were concentrated in vacuo, and the residue was Kégelrohr distilled to give a clear oil (5.46 g, 99.8%). The oil was dissolved in acetonitrile and concentrated HCl added to form the salt which was recrystallized from i-PrOH and dried in vacuo to give the product as a White powder (4.02 g, m.p. 185°–188° C.).

EXAMPLE 23

1-(5-Ethoxy-4-pyrimidinyl)piperazine

5-Ethoxypyrimidine

Sodium (2.89 g. 125.8 mmol) was dissolved in ethanol (110 mL) and 5-bromopyrimidine (10.0 g, 62.9 mmol) added. The reaction was heated at 120° in an autoclave for 17 h and then allowed to stand at 23° for 60 h. The ethanol was removed under reduced pressure and water (5 mL) added to the concentrate. The aqueous phase was extracted with $CH_2Cl_2$ (4×100 mL). The combined organic extracts were washed with saturated NaCl solution, dried with anhydrous $K_2CO_3$, filtered, and concentrated under reduced pressure. Silica gel chromatography (Hexane/EtOAc; 70:30) of the concentrate yielded 5-ethoxypyrimidine (2.00 g, 25.6%).

5-Ethoxypyrimidine N-oxide

To a solution of 5-ethoxypyrimidine (2.00 g, 16.1 mmol) in $CH_2Cl_2$ (100 mL) was added 3-chloroperoxybenzoic acid, 50–60% tech. grade, (6.13 g, 17.7 mmol) and the reaction stirred at 23° C. for 18 h. The reaction was extracted with water (2 mL) containing $Na_2CO_3$ (1.71 g, 16.1 mmol). The organic phase was dried with anhydrous $K_2CO_3$, filtered, and concentrated under reduced pressure to afford the N-oxide (1.75 g, 78%).

4-Chloro-5-ethoxypyrimidine

To a solution of triethylamine (1.90 g, 18.6 mmol) and phosphorous oxychloride (2.87 g, 18.6 mmol) in $CHCl_3$ (60 mL) was added 5-ethoxypyrimidine N-oxide (1.75 g, 12.5 mmol) portionwise. After the addition was complete, the reaction was heated at reflux for 3 h. Upon cooling the mixture to 0° C., $CHCl_3$ (60 mL) and water (10 mL) were added followed by portionwise addition of $NaHCO_3$ (3.15 g, 37.5 mmol). After the effervescence had ceased, the organic phase was separated, dried with $MgSO_4$, filtered, and concentrated under reduced pressure to afford the chloro product (1.98 g) which was used without further purification.

4-(Ethoxycarbonyl)-1-(5-ethoxy-4-pyrimidinyl)piperazine

A mixture of 4-chloro-5-ethoxypyrimidine (1.98 g, 12.5 mmol), ethyl 1-piperazinecarboxylate (5.93 g, 37.5 mmol) and micropulverized $K_2CO_3$ (5.18 g, 37.5 mmol) was heated at reflux in $CH_3CN$ (75 mL) for 4 h. Upon cooling to 23° C., the solvent was removed under reduced pressure. The residue was dissolved in $CH_2Cl_2$ and washed with water (5 mL). The organic phase was dried with anhydrous $K_2CO_3$, filtered, and concentrated under reduced pressure. Silica gel chromatography (CH$_2$Cl$_2$/MeOH;98:2) of the concentrate yielded product (2.29 g, 65%).

1-(5-Ethoxy-4-pyrimidinyl)piperazine

To a KOH solution (10N, 20 mL) was added 4-(ethoxycarbonyl)-1-(5-ethoxy-4-pyrimidinyl)piperazine (2.29 g, 8.18 mmol). The reaction was heated at reflux for 24 h after which time the water was removed under reduced pressure. The residue was dissolved in CH$_2$Cl$_2$, washed with saturated NaCl solution, dried with anhydrous K$_2$CO$_3$, filtered, and concentrated under reduced pressure. Silica gel chromatography (CH$_2$Cl$_2$/MeOH/NH$_4$OH;95:5:0.5) of the concentrate yielded III (0.71 g, 42%).

EXAMPLE 24

4-(5-Methoxy-4-pyrimidinyl)-2-methyl-piperazine—Method 1

A mixture of 2-methylpiperazine (27.74 g. 0.28 mole) and 4-chloro-5-methoxy-pyrimidine (8.0 g, 0.06 mole) was heated in a Parr bomb at 100° C. for 1.5 h. The reaction mixture was dissolved in CH$_2$Cl$_2$ and extracted with 5% NaHCO$_3$ and H$_2$O. The organic phase was dried with K$_2$CO$_3$, filtered, and concentrated under reduced pressure. Silica gel chromatography (CH$_2$Cl$_2$:MeOH:NH$_4$OH; 93:7:0.7) of the concentrate afforded product (9.02 g, 78.2%). Treatment of the base (1.0 g) with ethanolic HCl and crystallization from i-PrOH/EtOH yielded the hydrochloride salt (0.45 g, 32.1%, m.p. 191°-193° C.).

4-(5-Methoxy-4-pyrimidinyl)-2-methyl-piperazine—Method 2

A solution of 2-methylpiperazine (20 g) in water (100 mL) was reacted with solid 4,6-dichloro-5-methoxypyrimidine (5.00 g, 27.9 mmol) in a procedure similar to that given for Method 2 of Example 21. After hydrogenation and filtration of the catalyst, the product was extracted from the filtrate with CH$_2$Cl$_2$. The extracts were concentrated in vacuo, and the residue was Kügelrohr distilled to give a clear oil (5.46 g, 99.8%). The oil was dissolved in acetonitrile and concentrated HCl added to form the salt which was recrystallized from i-PrOH and dried in vacuo to give the product as a white powder (4.02 g, m.p. 1.85°-188° C.

Product Compounds of Formula I

EXAMPLE 25

1-[3-(5-Ethanesulfonylamino-1H-indol-3-yl)propyl]-4-(5-methoxy-4-pyrimidinyl)-3-methylpiperazine To a solution of 3-(5-ethanesulfonylamino-1H-indol-3-yl)propyl methanesulfonate (0.75 g, 2.1 mmol) in 15 mL of acetonitrile was added diisopropylethylamine (0.54 g, 4.2 mmol), potassium iodide (0.05 g, 0.3 mmol), t-butylammonium hydrogensulfate (0.04 g, 0.1 mmol), and 4-(5-methoxy-4-pyrimidinyl)-3-methylpiperazine (0.87 g, 4.2 mmol). The reaction was heated to reflux for 20 h. The reaction was concentrated in vacuo and the residue treated with 5% NaHCO$_3$ and extracted with three portions of ethyl acetate. The combined organic layers were washed with a saturated NaCl solution, dried over anhydrous K$_2$CO$_3$, filtered, and concentrated in vacuo. Silica gel chromatography (98:2 CH$_2$Cl$_2$:MeOH) of the residue afforded 0.32 g (32%) of the desired material. The hydrochloride salt was prepared by addition of ethanolic HCl. The salt was recrystallized from ethanol to yield 1-[3-(5-ethanesulfonylamino-1H-indol-3-yl)propyl]-4-(5-methoxy-4-pyrimidinyl)-3-methylpiperazine hydrochloride hydrate (0.15 g, 39%), m.p. 212°-214° C. Analysis calcd. for C$_{23}$H$_{32}$N$_6$O$_3$S.2 HCl.0.4 H$_2$O. 0.3 EtOH: C., 50.04; H, 6.52; N, 14.84, found: C., 50.12; H, 6.27; N, 14.90.

EXAMPLE 26

1-[3-[5-[Methyl(trifluoromethanesulfonyl)amino]-1H-indol-3-yl]propyl]-4-(5-methoxy-4-pyrimidinyl) piperazine m.p. >230° C. was prepared in a similar manner starting from 5-trifluoromethanesulfonylamino-1H-indole. Analysis calcd. for C$_{22}$H$_{27}$F$_3$N$_6$O$_3$S.2.0 HCl: C, 45.14; H, 5.00; N, 14.36; found: C, 44.75; H, 4.90; N, 14.42.

EXAMPLE 27

1-[3-[5-[[(Phenylmethoxy)carbonyl]amino]-1H-indol-3-yl]propyl]-4-(5-methoxy-4-pyrimidinyl)piperazine A solution of 3-[5-[(phenylmethoxycarbonyl)amine]-1H-indol-3-yl]propyl 4-methylbenzenesulfonate (0.54 g, 1.13 mmol), 4-(5-methoxy-4-pyrimidinyl)piperazine (0.44 g, 2.26 mmol), diisopropylethylamine (0.29 g, 2.26 mmol), potassium iodide (0.19 g, 1.13 mmol), and t-butylammonium hydrogensulfate (0.02 g, 1.13 mmol) in CH$_3$CN (10 mL) was heated at reflux for 20 h. After concentrating the reaction in vacuo, the residue was treated with 5% NaHCO$_3$ and extracted with four portions of CH$_2$Cl$_2$. The combined organic phases were washed with saturated NaCl, dried with K$_2$CO$_3$, filtered, and concentrated in vacuo. Silica gel chromatography (CH$_2$Cl$_2$:MeOH 96:4 ) of the concentrate afforded 1-8 3-[5-[[(phenylmethoxy)carbonyl]amino]-1H-indol-3-yl]propyl]-4-(5-methoxy-4-pyrimidinyl)piperazine (0.44 g, 77%), mp 174°′175° C. Analysis calcd. for C$_{28}$H$_{32}$N$_6$O: C, 67.19; H, 6.45; N, 16.79, found: C, 67.05; H, 6.47; N, 16.88.

EXAMPLE 28

4-(5-Methoxy-4-pyrimidinyl)-1-[3-[5-[[(methylamino) sulfonyl]methyl]-1H-indol-3-yl]propyl]piperazine To a solution of crude 3-]5-]](methylamino)sulfonyl]-methyl]-1H-indol-3-yl]propyl methanesulfonate (18.3 mmol, 1.0 equiv.) in 225 mL of anhydrous acetonitrile was added 3.30 g (18.3 mmol, 1.0 equiv.) of potassium iodide, 3.81 mL (21.9 mmol, 1.2 equiv.) of N,N-diisopropylethylamine and 3.89 g (20.1 mmol, 1.1 equiv.) of 1-(5-methoxy-4-pyrimidinyl)piperazine. The mixture was heated to reflux for sixteen hours. The reaction mixture was concentrated in vacuo and the residue was taken up in 500 mL of chloroform. The organic layer was washed with 100 mL portions of 10% potassium carbonate and saturated aqueous sodium chloride. The organic layer was dried over anhydrous magnesium sulfate, filtered and concentrated in vacuo to yield an oil. The oil was purified by chromatography on silica gel using 5% methanol in methylene chloride containing 0.5% concentrated aqueous ammonium hydroxide followed by chromatography on silica gel using 20% methanol in ethyl acetate to obtain 4.83 g (58%) of 4-(5-methoxy-4-pyrimidinyl)-1-[3-[5-[[(methylamino)-sulfonyl]methyl]-1H-indol-3-yl]propyl]piperazine. The hydrochloride salt was prepared by addition of 3N ethanolic HCl. Two recrystallizations from hot methanol gave 4.05 g (68%) of 4-(5-methoxy-4-pyrimidinyl)-

1-[3-[5-[[(methylamino)sulfonyl]methyl]-1H-indol-3-yl]propyl]-piperazine hydrochloride, m.p. 170° C. (d). Elemental analysis calculated for $C_{22}H_{30}N_6O_3S/3$ HCl: C, 46.52; H, 5.86; N, 14.80; found: C., 46.14; H, 6.22; N, 14.51.

EXAMPLE 29

4-(5-Methoxy-4-pyrimidinyl)-1-[3-5-[[(methylamino)-sulfonyl]methyl]-1H-indol-3-yl]propyl]-3-methylpiperazine hydrochloride hydrate In a similar manner the 4-(5-methoxy-4-pyrimidinyl)-3-methylpiperazine derivative was synthesized by substituting 1-(5-methoxy-4-pyrimidinyl)-2-methylpiperazine for 1-(5-methoxy-4-pyrimidinyl)piperazine in the alkylation step: $C_{23}H_{32}N_6O_3S/2.8$ HCl/0.8 $C_3H_8O$, m.p. 148° C. (d). Elemental analysis calculated: C, 48.99; H, 6.67; N, 13.49; found: C, 48.98; H, 6.77; N, 13.27.

EXAMPLE 30

1-[3-[5-[[(Dimethylamino)sulfonyl]methyl]-1H-indol-3-yl]propyl]-4-(5-methoxy-4-pyrimidinyl)piperazine To a solution of crude 3-[5-[[(dimethylamino)sulfonyl]methyl]-1H-indol-3-yl]propyl methanesulfonate (1.4 mmol, 1.0 equiv.) in 10 mL of anhydrous acetonitrile was added 0.225 g (1.50 mmol, 1.1 equiv.) of sodium iodide, 0.26 mL (1.50 mmol, 1.1 equiv.) of N,N-diisopropylethylamine and 0.291 g (1.50 mmol, 1.1 equiv.) of 1-(5-methoxy-4-pyrimidinyl)piperazine. The mixture was heated to reflux for sixteen hours. The reaction mixture was concentrated in vacuo and the residue was taken up in 50 mL of ethyl acetate. The organic layer was washed with a 10 mL portion of 10% potassium carbonate. The organic layer was dried over anhydrous sodium sulfate, filtered and concentrated in vacuo to yield an oil. The oil was purified by chromatography on silica gel using 5% methanol in methylene chloride containing 0.5% concentrated aqueous ammonium hydroxide to obtain 0.403 g (62%) of 1-[3-[5-[[(dimethylamino)sulfonyl]-methyl]-1H-indol-3-yl]propyl]-4-(5-methoxy-4- pyrimidinyl)piperazine. The hydrochloride salt was prepared by addition of 3N ethanolic HCl. Two recrystallizations from methanol gave 0.323 g (64%) of 1-[3-[5-[[(dimethyl-amino)sulfonyl]methyl]-1H-indol-3-yl]propyl]-4-(5-methoxy-4-pyrimidinyl)piperazine hydrochloride hydrate, m.p. 210° C. (d). Elemental analysis calculated for $C_{23}H_{32}N_6O_3S/3$ HCl/0.5 $H_2O$: C, 46.74; H, 6.14; N, 14.22; found: C., 46.82; H, 6.42; N, 14.09.

EXAMPLE 31

4-(5-Methoxy-4-pyrimidinyl)-1-[[5-[[(methylsulfonyl)amino]methyl]-1H-indol-3-yl]propyl]piperazine To a solution of crude 3-[5-[[(methylsulfonyl)amino]-methyl]-1H-indol-3-yl]propylmethanesulfonate (15.1 mmol, 1.0 equiv.) in 200 mL of anhydrous acetonitrile were added 2.51 g (15.1 mmol, 1.0 equiv.) of potassium iodide, 3.15 mL of N,N-diisopropylethylamine and 3.23 g of 1-(5-methoxy-4-pyrimidinyl)piperazine. The mixture was heated to reflux for 48 hours. The reaction mixture was cooled to room temperature, filtered and concentrated. The residue was dissolved in 250 mL of chloroform, washed with 50 mL portions of 10% aqueous potassium carbonate and saturated aqueous sodium chloride. The organic layer was dried over anhydrous magnesium sulfate, filtered and concentrated in vacuo to yield an oil. Chromatography on silica gel using 7.5% methanol in methylene chloride containing 0.75% concentrated aqueous ammonium hydroxide gave 3.93 g (57%) of 4-(5-methoxy-4-pyrimidinyl)-1-[[5-[[(methylsulfonyl)amino]methyl]-1H-indol-3-yl]propyl]piperazine. The hydrochloride was prepared by addition of 3N ethanolic HCl to an ethanolic solution of the base. Recrystallization from ethanol followed by drying in vacuo at 65° C. gave 0.268 g (53%) of the hydrochloride ethanolate: $C_{22}H_{30}N_6O_3S/2.4$ HCl/0.4 $C_2H_6O$, m.p. 204°–206° C. Elemental analysis calculated C., 48.51; H, 6.21; N, 14.89; found: C., 48.59; H, 6.21; N, 14.95.

EXAMPLE 32

4-(5-Methoxy-4-pyrimidinyl)-1-[[5-[[methyl(methylsulfonyl)amino]methyl]-1H-indol-3-yl]propyl]piperazine To a solution of 1.93 g (4.21 mmol, 1.0 equiv.) of 4-(5-methoxy-4-pyrimidinyl)-1-[[5-[[(methylsulfonyl)amino]methyl]-1H-indol-3-yl]propyl]piperazine in 84 mL of anhydrous THF at −b 78° C. was added 1.9 mL (4.41 mmol, 1.05 equiv.) of a 2.32M solution of nBuLi in hexane dropwise. A precipitate formed during the addition. After the addition was complete the reaction mixture was allowed to stir for forty minutes at −78° C. The reaction was then placed in an ice bath and 0.275 mL (4.41 mmol, 1.05 equiv.) of methyl iodide added dropwise neat. The reaction was allowed to warm slowly in the ice bath to room temperature over sixteen hours. The reaction mixture was diluted with 250 mL of ethyl acetate and washed with 50 mL portions of 10% aqueous potassium carbonate and saturated aqueous sodium chloride. The organic layer was dried over anhydrous magnesium sulfate, filtered and concentrated in vacuo to yield an oil. The oil was chromatographed with 5% methanol in methylene chloride containing 0.5% concentrated aqueous ammonium hydroxide to yield 1.1 g of a solid. The solid was recrystallized to yield 0.760 g (38%) of pure 4-(5-methoxy-4-pyrimidinyl)-1-[[5-[[methyl-(methylsulfonyl)amino]methyl]-1H-indol-3-yl]propyl]piperazine, $C_{22}H_{30}N_6O_3S$, m.p. 164°–165° C. Elemental analysis calculated: C, 58.45; H, 6.82; N, 17.78; found: C., 58.12; H, 6.75; N, 17.56.

EXAMPLE 33

1-[[5-[[Ethyl(methylsulfonyl)amino]methyl]-1H-indol-3-yl]propyl]-4-(5-methoxy-4-pyrimidinyl)piperazine In a similar manner to Example 32 the 1-[[5-[[ethyl(-methylsulfonyl)amino]methyl]-1H-indol-3-yl]propyl]-4-(5-methoxy-4-pyrimidinyl)piperazine was synthesized by utilizing ethyl iodide in the alkylation step: $C_{23}H_{32}N_6O_3S/3.7$ HCl, m.p. 197° C. (d). Elemental analysis calculated: C, 45.47; H, 5.92; N, 13.83; found: C, 45.32; H, 6.10; N, 13.73.

EXAMPLE 34

4-(5-Methoxy-4-pyrimidinyl)-1-[[5-*[phenylmethyl (methylsulfonyl)amino*1-methyl]-1H-indol-3-yl]propyl]-piperazine In a similar manner to Example 32 4-(5-methoxy-4-pyrimidinyl)-1-[[5-[[phenylmethyl(methylsulfonyl)amino]-methyl]-1H-indol-3-yl]propyl]piperazine was synthesized by utilizing benzyl bromide in the alkylation step: $C_{29}H_{36}N_6O_3S/1.1$ HCl, m.p. 203°–204° C. Elemental analysis calculated: C, 59.16; H, 6.35; N, 14.27; found: C, 59.04; H, 6.38; N, 14.11.

EXAMPLE 35

1-[[5-[[(Ethylsulfonyl amino]methyl]-1H-indol-3-yl]-propyl]-4-(5-methoxy-4-pyrimidinyl)piperazine In a similar manner to Example 32 1-[[5-[[(ethylsulfonyl)amino]methyl]-1H-indol-3-yl]propyl]-4-(5-methoxy-4-pyrimidinyl)piperazine was synthesized by utilizing ethanesulfonyl chloride in the sulfonylation step: $C_{23}H_{32}N_6O_3S/2.1\ C_4H_4O_4/0.6\ H_2O$, m.p. 136° C. (d). Elemental analysis calculated: C, 51.70; H, 5.73; N, 11.38; found: C, 51.32; H, 5.70; N, 11.54.

EXAMPLE 36

1-[[5-[[(Methylsulfonyl)amino[methyl]-1H-indol-3-yl]propyl]-4-(5-methoxy-4-pyrimidinyl)-3-methylpiperazine In a similar manner to Example 32 1-[[5-[[(methyl-sulfonyl)amino]methyl]-1H-indol-3-yl]propyl]-4-(5-methoxy-4-pyrimidinyl)-3-methylpiperazine was synthesized by utilizing 1-(5-methoxy-4-pyrimidinyl)-2-methylpiperazine in the coupling step: $C_{23}H_{32}N_6O_3S/2.1\ HCl/0.4\ C_2H_6O$, m.p. 210°–214° C. Elemental analysis calculated: C, 50.36; H, 6.48; N, 14.81; found: C, 50.34; H, 6.47; N, 14.74.

EXAMPLE 37

1-[[5-[[(Ethylsulfonyl)amino[methyl]-1H-indol-3-yl]propyl -4-(5-methoxy-4-pyrimidinyl)-3-methylpiperazine In a similar manner to Example 32 1-[[5-[[(ethylsulfonyl)amino]methyl]-1H-indol-3-yl]propyl]-4-(5-methoxy-4-pyrimidinyl)-3-methylpiperazine was synthesized by utilizing 1-(5-methoxy-4-pyrimidinyl)-2-methylpiperazine in the coupling step and ethanesulfonyl chloride in the sulfonylation step: $C_{24}H_{34}N_6O_3S/2.9$ HCl, m.p. 202°–210° C. Elemental analysis calculated: C, 48.66; H, 6.28; N, 14.19; found: C, 48.41; H, 6.35; N, 13.93.

EXAMPLE 38

4-(5-Methoxy-4-pyrimidinyl)-1-[[5-[[methyl(ethylsulfonyl)amino]-methyl]-1H-indol-3-yl]propyl]piperazine In a similar manner to Example 32 4-(5-methoxy-4-pyrimidinyl)-1-[[5-[[methyl(ethylsulfonyl)amino]methyl]-1H-indol-3-yl]propyl]piperazine was synthesized by utilizing methyl iodide in the alkylation step and ethanesulfonyl chloride in the sulfonylation step: $C_{24}H_{34}N_6O_3S/C_4H_6O_4$, m.p. 113°–115° C. Elemental analysis calculated: C., 55.61; H, 6.67; N, 13.90; found: C., 55.43; H, 6.67; N, 13.74. cl EXAMPLE 39

4-(5-Methoxy-4-pyrimidinyl)-1-[[5-[[phenylmethyl(ethylsulfonyl)amino]-methyl]-1H-indol-3-yl]propyl]piperazine In a similar manner to Example 32 4-(5-methoxy-4-pyrimidinyl)-1-[[5-[[phenylmethyl(ethylsulfonyl)amino]-methyl]-1H-indol-3-yl]propyl]piperazine was synthesized by utilizing benzyl bromide in the alkylation step and ethanesulfonyl chloride in the sulfonylation step: $C_{30}H_{38}N_6O_3S/1.2\ C_4H_6O_4$, m.p. 73°–75° C. Elemental analysis calculated: C, 59.34; H, 6.47; N, 11.93; found: C, 59.02; H, 6.17; N, 11.89.

EXAMPLE 40

1-[[5-[[(Acetyl)amino]methyl]-1H-indol-3-yl]propyl]-4-(5-methoxy-4-pyrimidinyl)piperazine In a similar manner to Example 32 1-[[5-[[(acetyl)amino]-methyl]-1H-indol-3-yl]propyl]-4-(5-methoxy-4-pyrimidinyl)-piperazine was synthesized by utilizing acetic anhydride for acylation rather than a sulfonyl chloride for sulfonylation: $C_{23}H_{30}N_6O_2/2.8\ HCl/1.2\ H_2O$, m.p. 169°–174° C. Elemental analysis calculated: C, 50.57; H, 6.50; N, 15.39; found: C, 50.22; H, 6.87; N, 15.25.

EXAMPLE 41

1-[3-(5-Cyano-1H-indol-3-yl)propyl]-4-(5-methoxy-4-pyrimidinyl piperazine

To a solution of 3-(5-cyano-1H-indol-3-yl)propyl methanesulfonate (2.35 mmol, 1.0 equiv.) in 25 mL of anhydrous acetonitrile was added 0.874 g (4.5 mmol, 1.5 equiv.) of (5-methoxy-4-pyrimidinyl)piperazine and 1.0 mL of N,N-diisopropylethylamine. The mixture was heated to reflux for thirteen hours. The solution was cooled, diluted with 100 mL of chloroform and washed once with 20 mL of 10% aqueous sodium carbonate. The organic layer was separated, dried over anhydrous sodium sulfate, filtered and concentrated. The residue was chromatographed on silica gel using 5% methanol in methylene chloride containing 0.5% concentrated aqueous ammonium hydroxide to yield 0.375 g (42%, two steps) of 1-[3-(5-cyano-1H-indol-3-yl) propyl]-4-(5-methoxy-4-pyrimidinyl)piperazine pure by $^1$H NMR analysis.

EXAMPLE 42

1-[3-(5-Aminocarbonyl-1H-indol-3-yl)propyl]-4-(5-methoxy-4-pyrimidinyl)piperazine To a solution of 1.19 g (3.17 mmol, 1.0 equiv.) of 1-[3-(5-cyano-1H-indol-3-yl)propyl]-4-(5-methoxy-4-pyrimidinyl)piperazine in 16 mL of ethanol was added a solution of 1.85 g (33.0 mmol, 10.4 equiv.) of potassium hydroxide in 16 mL of ethanol. The solution was heated to reflux for 16 hours. TLC. indicated the reaction was less than 50% complete. The reaction mixture was diluted with 150 mL of ethyl acetate and washed once with 25 mL of saturated aqueous sodium bicarbonate. The organic layer was separated, dried over anhydrous sodium sulfate, filtered and concentrated to yield 1.22 g of an oil. The oil was chromatographed on silica gel using 10% methanol in methylene chloride containing 1% concentrated aqueous ammonium hydroxide to yield 0.293 g (23%) of 1-[3-(5-aminocarbonyl-1H-indol-3-yl)propyl]-4-(5-methoxy-4-pyrimidinyl)piperazine. Conversion to the HCl salt gave $C_{21}H_{24}N_6O/2.8\ HCl/0.7\ H_2O$, mp. 220°–225° C.(d). Elemental anal. calcd: C, 51.35; H, 5.79; N, 17.11; found: C., 51.61; H, 6.08; N, 16.82.

EXAMPLE 43

3-[3-[4-(5-Methoxy-4-pyrimidinyl)-1-piperazinyl]-propyl]-5-aminoindole

5-Nitro-3-(3-bromopropyl)indole

To a solution of triphenylphosphine (6.70 g, 0.025 mol) in 80 mL of acetonitrile was added a solution of 5-nitro-3-(3-hydroxypropyl)indole (4.30 g, 0.020 mol) in 75 mL of acetonitrile, followed by a solution of CBr$_4$ (9.00 g, 0.027 mol) in 25 mL of acetonitrile, at 0° C.

under Ar. The mixture was stirred at room temperature for 3 h and then it was evaporated and the residue was chromatographed (SiO$_2$/EtOAc-hexane, 1:9 then 1:4) to give the bromo compound (4.60 g, 84%) as a solid, m.p. 92°–95° C.

3-[3-[4-(5-Methoxy-4-pyrimidinyl)-1-piperazinyl]-propyl]-5-nitroindole

A mixture of 5-nitro-3-(3-bromopropyl)indole (0.57 g, 2.0 mmol), 1-(5-methoxy-4-pyrimidyl) piperazine (0.47 g, 2.4 mmol), KI (0.40 g, 2.4 mmol) and diisopropylethylamine (1.75 mL, 10.0 mmol) in 20 mL of acetonitrile was refluxed under Ar for 6h. The cooled reaction mixture was diluted with ethyl acetate and washed (H$_2$O, brine). The aqueous wash was back-extracted with CH$_2$Cl$_2$ and the organic phase was washed (H$_2$O, brine). The combined organic phases were dried (Na$_2$SO$_4$) and evaporated, and the residue was chromatographed (SiO$_2$/CH$_2$Cl$_2$ -MeOH, 95:5) to give a solid. This material was triturated with CH$_2$Cl$_2$ -hexane to give the title compound (0.55 g, 70%) as a yellow solid, m.p. 163°–166° C.

3-[3-[4-(5-Methoxy-4-pyrimidinyl)-1-piperazinyl]-propyl]-5-aminoindole

To a solution of 3-[3-[4-(5-methoxy-4-pyrimidyl)-1-piperazinyl]propyl]-5-nitroindole (0.550 g, 1.39 mmol) in a mixture of ethanol (120 mL) and THF (40 mL) was added 10% palladium-on-charcoal (0.30 g) and the mixture was hydrogenated in a Parr shaker at 40 psi for 18 h. The mixture was then filtered through Celite and the cake was washed with additional ethanol-THF. Evaporation of the filtrate gave the essentially pure title compound (0.557 g, 100 %) as a brown foam. A sample of this material (0.143 g ) was treated with excess methanolic HCl and the resulting solution was diluted with acetone to give a precipitate. The precipitate was filtered and then it was crystallized from ethanol to give 0.100 g of a purplish solid, m.p. 192° C. (dec). IR (KBr) 3410, 3200, 1630, 1540 cm$^{-1}$; $^1$H NMR (DMSO-d$_6$, 200 MHz) δ11.22 (br s, 1H), 10.20 (br s, 2H), 8.60 (d, 1H), 8.20 (s, 1H), 7.55 (d, J=1.6 Hz, 1H), 7.55 (d, J=1.6 Hz, 1H), 7.45 (d, J=8.6 Hz, 1H), 7.35 (d, J=2.1 Hz, 1H), 7.07 (dd, J=8.6, 1.9 Hz, 1H), 4.89–4.82 (m, 2H), 3.91 (s, 3H), 3.8–3.0 (br m, 8H), 2.76 (m, 2H), 2.12 (br m, 2H). Anal. Calcd. for C$_{20}$H$_{26}$N$_6$O.4HCl.H$_2$O: C., 45.29; H, 6.08; N, 15.85. Found: C., 45.32; H, 5.97; N, 15.59.

EXAMPLE 44

3-[3-[4-(5-Methoxy-4-pyrimidinyl)-1-piperazinyl]-propyl]-5-(methyl-carbamoyl)oxindole To a solution of 3-[3-[4-(5-methoxy-4-pyrimidinyl)-1-piperazinyl]propyl]-5-hydroxyindole (0.170 g, 0.46 mmol) in 6 mL of CH$_2$Cl$_2$ was added methyl isocyanate (60 μL, 1.0 mmol) and the mixture was stirred at room temperature for 4 days. The mixture was then evaporated and the resulting pinkish-gray foam was triturated with isopropanol-ether to give a light grey solid. This material was chromatographed (SiO$_2$/EtOAc-MeOH, 95:5; then 90:10) to give the title compound (0.120 g, 60%) as a light gray solid, m.p. 120°–122° C. IR (KBr) 3400, 3220, 1730 cm$^{-1}$; $^1$H NMR (CDCl$_3$, 200 MHz) δ8.33 (s, 1H), 8.06 (br s, 1H), 7.88 (s, 1H), 7.34–7.26 (m, 2H), 6.99–6.91 (m, 2H), 5.00 (br m, 1H), 3.85 (s, 3H), 3.79 (t, J=4.7 Hz, 4H), 2.91 (d, J=4.8 Hz, 3H), 2.75 (t, J=7.4 Hz, 2H), 2.54 (t, J=4.8 Hz, 4H), 2.45 (t, J=7.6 Hz, 2H), 2.04–1.83 (m, 2H) Anal. Calcd. for C$_{22}$H$_{28}$N$_6$O$_3$.0.8H$_2$O: C, 60.20; H, 6.80; N, 19.15. Found: C, 60.13; H, 6.40; N, 18.75.

EXAMPLE 45

3-[3-[4-(5-Methoxy-4-pyrimidinyl)-1-piperazinyl]-propyl]-5-(cyanomethyl)oxyindole To a suspension of NaH (60% in oil, 0.020 g, 0.5 mmol) in 10 mL of dry THF was added a suspension of 3-[3-[4-(5-methoxy-4-pyrimidyl)-1-piperazinyl]propyl]-5-hydroxyindole (0.183 g, 0.5 mmol) in 20 mL of THF, at room temperature under Ar. After 30 min gas evolution had ceased and a clear solution was obtained. To this solution was added a solution of chloroacetonitrile (35 μL, 0.55 mmol) in 5 mL of dry THF, and the mixture was stirred at room temperature for 2 h and then refluxed for 1½ h. The cooled mixture was diluted with CH$_2$Cl$_2$ , washed (water, brine), dried (Na$_2$SO$_4$) and evaporated to give a foam. Column chromatography (SiO$_2$/CH$_2$Cl$_2$ -MeOH, 95:5; then CH$_2$Cl$_2$ -MeOH-NH$_4$OH, 95:4.5;0.5) afforded the title compound (0.150 g, 75%) as a foam. This material was treated with excess methanolic HCl and the solution was evaporated to give a glass. Trituration with MeOH-EtOH (1:9) gave the hydrochloride (0.110 g) as an off-white solid, m.p. 198°–200° C. (dec): IR (KBr) 3400, 3220, 1630 cm$^{-1}$; $^1$H NMR (DMSO-d$_6$, 200 MHz) δ11.39 (br s, 1H), 10.87 (br s, 1H), 8.61 (s, 1H), 8.20 (s, 1H), 7.30 (d, J=8.8 Hz, 1H), 7.24 (d, J=2.4 Hz, 1H), 7.22 (d, J=2.0 Hz, 1H), 6.83 (dd, J=8.7, 2.4 Hz, 1H), 5.16 (s, 2H), 4.90–4.83 (m, 2H), 3.90 (s, 3H), 3.70–3.36 (m, 4H), 3.13 (br s, 4H), 2.75 (m, 2H), 2.12 (m, 2H). Anal. Calcd. for C$_{22}$H$_{26}$N$_6$O$_2$.2.5 HCl.0.3 C$_2$H$_6$O: C,53.07; H, 5.97; N, 16.43. Found; C, 53.26; H, 5.70; N, 16.11.

EXAMPLE 46

3-[3-[4-(5-Methoxy-4-pyrimidinyl)-1-piperazinyl]-propyl]-5-(carboxamidomethyl)oxyindole To a suspension of NaH (60% in oil, 0.020 g, 0.5 mmol) in 5 mL of dry THF was added a suspension of 3-[3-[4-(5-methoxy-4-pyrimidinyl)-1-piperazinyl]propyl]-5-hydroxyindole (0.184 g, 0.5 mmol) in 35 mL of dry THF, and the mixture was stirred at room temperature under Ar for 30 min. To the resulting clear solution was added a solution of 2-chloroacetamide (0.047 g, 0.5 mmol) in 5 mL of THF and the mixture was kept at room temperature for 2 h and then it was refluxed for 2 h. The cooled mixture was diluted with ethyl acetate, and then it was washed (water, brine), dried (Na$_2$SO$_4$) and evaporated. The residue was chromatographed (SiO$_2$/THF) to give impure starting material (0.117 g). Further elution afforded the title compound (0.100 g, 47%) as a gum. This material was treated with excess methanolic HCl and the solution was then evaporated and the residue was crystallized from methanol-ether to give the hydrochloride (0.095 g) as a grayish solid, m.p. 90° C.: IR (KBr) 3400, 3250, 1680, 1630 cm$^{-1}$; $^1$H NMR (DMSO-d$_6$, 200 MHz) δ11.55 (br s, 1H), 10.76 (br s, 1H), 8.69 (s, 1H), 8.21 (s, 1H), 7.49–7.40 (br m, 2H), 7.25 (d, J=8.6 Hz, 1H), 7.16 (d, J=2.1 Hz, 1H), 7.05 (d, J=2.2 Hz, 1H), 6.81 (dd, J=8.7, 2.3 Hz, 1H), 4 99–4.92 (br m, 2H), 4.41 (s, 2H), 3.91 (s, 3H), 4.3–3.5 (m, 4H), 3.11 (br s, 4H), 2.72 (m, 2H), 2.10 (br s, 2H). Anal. Calcd. for C$_{22}$H$_{28}$N$_6$O$_3$.3HCl.H$_2$O: C, 47.87; H, 6.03; N, 15.23. Found: C., 48.24; H, 5.89; N, 14.83.

EXAMPLE 47

1-[3-[5-acetyl-1H-indol-3-yl]propyl]-4-(5-methoxy-4-pyrimidin yl)piperazine hydrochloride was prepared in the usual manner from 1-[5-acetyl-1H-indol-3-yl]-3-propanol. m.p. 215°–217° (d). Analysis calcd. for $C_{22}H_{27}N_5O_2 \cdot 2.7$ HCl: C, 53.72; H, 6.09; N, 14.24. found: C., 53.52; H, 6.23; N, 14.28.

EXAMPLE 48

4-(5-Methoxy-4-pyrimidinyl)-1-[3-[5-[2-(methylsulfonyl)methyl]-1H-indol-3-yl]propyl]piperazine m.p. 190°–195° C. Analysis calcd. for $C_{22}H_{29}N_5O_3S$. 3.0 HCl: C, 47.79; H, 5.84; N, 12.67; Found: C, 47.58; H, 5.96; N, 12.32.

EXAMPLE 49

4-(5-Methoxy-4-pyrimidinyl)-1-[3-[5-[2-(methylsulfonyl)methyl]-1H-indol-3-yl]propyl]-3-methylpiperazine m.p. 208°–210(d)° C. Analysis calcd. for $C_{23}H_{32}N_5O_3S$. 2.5 HCl: C, 50.25; H, 6.33; N, 12.47; Found: C., 50.17; H, 6.04; N, 12.58.

EXAMPLE 50

4-(5-Methoxy-4-pyrimidinyl)-1-[3-[5-[2-(methylsulfonyl)ethyl]-1H-indol-3-yl]propyl]piperazine m.p 153°–154° C. Analysis calcd. for $C_{23}H_{31}N_5O_3S$: C, 60.37; H, 6.83; N, 15.30; Found: C, 60.24; H, 6.79; N, 15.42.

EXAMPLE 51

4-(5-Methoxy-4-pyrimidinyl)-1-[3-[5-[2-(methylsulfonyl)ethyl]-1H-indol-3-yl]propyl]-3-methylpiperazine m.p. 220°–223° C. Analysis calcd. for $C_{24}H_{33}N_5O_3S$. 2.5 HCl: C, 51.22; H, 6.36; N, 12.44; Found: C, 51.20; H, 6.26; N, 12.36.

EXAMPLE 52

4-(5-Ethoxy-4-pyrimidinyl)-1-[3-(1H-indol-3-yl)propyl]piperazine hydrochloride hydrate A mixture of 3-(1H-indole-3-yl)propyl 4-methylbenzenesulfonate (0.87 g, 2.65 mmol), 1-(5-ethoxy-4-pyrimidinyl)piperazine (1.10 g, 5.29 mmol), micropulverized $K_2CO_3$ (0.73 g, 5.29 mmol), and tetrabutylammonium hydrogen sulfate (0.04 g, 0.13 mmol) in $CH_3CN$ (15 mL) was heated at reflux for 2.5 h under nitrogen atmosphere. The reaction was allowed to cool to 23° C. and stand for 16 h. The reaction was concentrated under reduced pressure and the residue was dissolved in $CH_2Cl_2$ and extracted with water. The organic phase was dried with anhydrous $K_2CO_3$, filtered, and concentrated under reduced pressure. Silica gel chromatography ($CH_2Cl_2$ /MeOH;98:2) of the residue afforded the free base (0.70 g, 72%) which was treated with ethanolic HC.l to yield I (0.85 g, 99%; mp >230° C.) after crystallization from EtOH/MeOH.

Anal. Calcd. for $C_{21}H_{27}N_5O \cdot 2HCl \cdot 0.7H_2O$:
C, 55.93; H, 6.80; N, 15.53; $H_2O$, 2.80.
Found: C, 55.67; H, 6.66; N, 15.40; $H_2O$, 2.50.

EXAMPLE 53

1-[3-(1H-indol-3-yl)butyl]-4-(5-methoxy-4-pyrimidinyl)piperazine

To a mixture of 1-(5-methoxy-4-pyrimidyl)piperazine (1.55 g, 8.0 mmol), triethylamine hydrochloride (1.10 g, 8.0 mmol) and $NaCNBH_3$ (1.76 g, 28 mmol) in 20 mL of dry THF was added a solution of 3-(3-oxobutyl)indole, J. Szmuskovicz, et al., *J. Am. Chem. Soc.* 79, 2819 (1957), (0.75 g, 4.0 mmol) in 5 mL of THF and the mixture was stirred at room temperature under Ar for 20 h. The reaction mixture was then poured into 10% saturated $NaHCO_3$ and extracted with ethyl acetate ($\times 2$). The organic extract was washed with $H_2O$ ($\times 2$) and then with 25 mL of 0.1N HCl. The resulting organic solution was extracted with 1N HCl ($\times 2$) and the aqueous phase was washed with $CH_2Cl_2$ ($\times 2$) and then it was cooled at 0° C. and basified with 50% aqueous NaOH. This gave a gummy precipitate which was extracted into ethyl acetate ($\times 4$) and the combined organic extract was then washed (brine), dried ($Na_2SO_4$) and evaporated to give a gum. Flash chromatography ($SiO_2$/acetonitrile-methanol; 95:5 then 80:20) of this material gave the pure product (968 mg, 66%) as a white foam.

The foam was taken up in $CH_2Cl_2$ and treated with excess ethanolic HCl. The solution was evaporated and the residue was again taken up in excess ethanolic HCl. Evaporation of the solution gave a light brown foam which was crystallized from hot methanol-acetone to give the hydrochloride (916 mg) as a white powder: m.p. 169°–72° C. (dec); IR (KBr) 3400, 1632, 1550, 1275 cm$^{-1}$; $^1$H nmr (200 MHz, CDCl$_3$) $\delta$11.68 (br s, 1H), 10.89 (s, 1H), 8.66 (s, 1H), 8.20 (s, 1H), 7.56 (d, J=7.4 Hz, 1H), 7.33 (d, J=7.7 Hz, 1H), 7.21 (d, J=2.3 Hz), 7.10–6.93 (m, 2H), 5.03–4.96 (m, 2H), 3.91 (s, 3H), 3.85–3.75 (m, 2H), 3.54–3.25 (m, 5H), 2.88–2.60 (m, 2H), 2.51–2.35 (m, 1H), 1.88–1.81 (m, 1H), 1.38 (d, J=6.5 Hz, 3H).

Anal. Calcd. for $C_{21}H_{27}N_5O \cdot 2HCl \cdot 1.4 H_2O$:
C, 54.50; H, 6.91 ; N, 15.11.
Found: C, 54.39; H, 6.93; N, 15.37.

EXAMPLE 54

3-[3-[4-(5-Methoxy-4-pyrimidinyl)-1-piperazinyl]pentyl]indole

A mixture of 3-(3-bromopentyl)indole (1.33 g, 5.0 mmol), 1-(5-methoxy-4-pyrimidyl)piperazine (2.00 g, 10 mmol) finely pulverized $K_2CO_3$ (0.70 g, 5.1 mmol) and finely pulverized KI (0.90 g, 5.1 mmol) in 20 mL of acetonitrile was heated to reflux under Ar for 5h. The cooled reaction mixture was diluted with EtOAc, washed ($H_2O$, brine), dried ($NO_2SO_4$) and evaporated to give a gum. Chromatographs of this material ($SlO_2$/EtOAc then 10% MeOH-EtOAc) affords the product (0.65 g, 34%) as a gum. This gum was taken up in ether and then methanolic HCl was added. The resulting solid was filtered, washed with Et$_2$O and dried in vacuo to give an off-white solid (0.50 g), mp 145° C. (dec); IR (KBr) 3400, 1633, 1550 cm$^{-1}$;

Anal. Calcd. for $C_{22}H_{29}N_5O \cdot 3HCl \cdot 0.75 H_2O$:
C, 52.59; H, 6.72; N, 13.94.
Found: C., 52.70; H, 6.34; N, 13.91.

EXAMPLE 55

1-[3-(5-Hydroxy-1H-indol-3-yl)propyl]-4-(5-methoxy-4-pyrimidinyl)piperazine

A mixture of 1-[3-(5-benzyloxy-1H-indol-3-yl)propyl]-4-(5-methoxy-4-pyrimidinyl)piperazine (Ex. 71; 1.40 g, 3.06 mmol) and 10% Pd(OH$_2$)/C (0.85 g) in 25 mL of ethanol was hydrogenated at 30–40 psi in a Parr shaker for 3.5 h. The mixture was filtered and then fresh catalyst (0.75 g) was added to the filtrate and hydrogenation was resumed at ca 45 psi for 22 h. The resulting mixture was filtered through Celite and the filtrate was evaporated to give a foam (0.995 g, 88%). The foam was taken up in in methanolic HCl, whereupon a white solid precipitated. The solid was filtered, washed with cold methanol and then ether, and dried in vacuo to give the hydrochloride as a slightly pinkish solid (0.59 g), mp 215° C.; IR (KBr) 3320 (Br) 1630, 1550 cm$^{-1}$; 7.07 (s, 1H), 6.80 (d, J=2.1 Hz, 1H), 6.59 (dd, J=2.2, 8.6 Hz, 1H), 4.91–4.84 (m, 2H), 3.90 (s, 3H), 3.8–3.4 (m, 7H), 3.2–3.0 (m, 4H), 2.69–2.62 (m, 2H), 2.2–2.0 (m, 2H).

Anal. Calcd. for $C_{20}H_{25}N_5O_2.2.25$ HCl:
C, 53.44; H, 6.11; N, 15.58.
Found: C, 53.30; H, 5.90; N, 15.40.

EXAMPLE 56

N-Butyl-3-[3-[4-(5-methoxy-4-pyrimidinyl)piperazin-1-yl]prop-1-yl]-1H-indole-5-carboxamide hydrochloride Sodium metal (0.84 g, 36.67 mmol) was dissolved in 15 mL of anhydrous methanol and n-butylamine (2.68 g, 36.67 mmol) at 0+ C. was added. A solution of methyl 3-[3-[4-[(5-methoxy-4-pyrimidinyl)piperazin-1-yl]prop-1-yl]-1H-indole-5-carboxylate (1.5 g, 3.67 mmol) in 5 mL of methanol was added. The reaction was heated at reflux for 24 hours. The reaction was cooled and quenched with 5 mL of water. The methanol was removed in vacuo. The residue was extracted with three 30 mL portions of ethyl acetate. The combined organic layers were dried over anhydrous sodium sulfate, filtered and concentrated in vacuo. Silica gel chromatography (94:6:0.5 $CH_2Cl_2$-MeOH-$NH_4OH$) of the concentrate yielded N-butyl-3-[3-[4-(5-methoxy-4-pyrimidinyl)piperazin-1-yl]prop-1-yl]-1H-indole-5-carboxamide (0.59 g, 36%). The hydrochloride salt was prepared from 0.59 g of N-butyl-3-[3-[4-(5-methoxy-4-pyrimidinyl)piperazin-1-yl]prop-1-yl]-1H-indole-5-carboxamide to yield the title compound (0.23 g, 36%): mp 180°–185° C. Anal. Calcd for $C_{25}H_{34}N_6O_2.2.0$ HCl: C, 57.36; H, 6.93; N, 16.05. Found: C, 57.01; H, 6.95; N, 15.98.

EXAMPLE 57

1-[3-[5-[(Trifluoromethyl)carbonyl]amino-1-H-indol-3-yl]propyl]-4-(5-methoxy-4-pyrimidinyl) piperazine hydrochloride To a solution of 1-[3-[5-amino-1-H-indol-3-yl]propyl]-4-(5-methoxy-4-pyrimidinyl) piperazine (0.5 g, 1.36 mmol) in methylene chloride (8 mL) at 0° C. was added trifluoroacetic anhydride (0.34 g, 1.63 mmol). The reaction mixture was allowed to warm to room temperature over 2 h. The solution was diluted with water, and the organic layer was dried (MgSO$_4$), filtered and concentrated in vacuo. Silica gel column chromatography (95:5 ethyl acetate-methanol) of the concentrate gave 1-[3-[5-[(trifluoromethyl)carbonyl]amino-1-H-indol-3-yl]propyl]-4-(5-methoxy-4-pyrimidinyl)piperazine (0.2 g, 32%). The free base (0.2 g, 0.43 mmol) was dissolved in a minimum volume of ethanol, and was converted to its hydrochloride salt with 2 mL of 3 N HCl in EtOH. The volatile components were removed in vacuo to give the title compound (0.19 g, 0.28 mmol, 67%), mp 295°–300° C. Anal. Calcd for $C_{22}H_{25}F_3N_6O_2.5.5$ HCl: C, 39.86; H, 4.64; N, 12.68. Found: C, 40.05; H, 5.03; N, 12.33.

EXAMPLE 58

1-[3-[5-[[(4-Methylphenyl)sulfonyl]amino]-1-H-indol-3-yl] propyl]-4-(5-methoxy-4-pyrimidinyl)piperazine oxalate p-Toluenesulfonyl chloride (0.30 g, 1.56 mmol) was dissolved in 2 mL of THF, and the solution was cooled to 0° C. A mixture of 1-[3-[5-amino-1-H-indol-3-yl]propyl]-4-(5-methoxy-4-pyrimidinyl)piperazine (0.5 g, 1.42 mmol), and triethylamine (0.16 g, 1.56 mmol) in 3 mL of THF was added to the p-toluenesulfonyl chloride solution. The solution was stirred at 0° C. for 30 min, warmed to 23° C. (1 h), and concentrated in vacuo. Silica gel column chromatography (95:5:0.5 $CH_2Cl_2$-MeOH-30% $NH_4OH$) of the concentrate gave 1-[3-[5-[[(4-methylphenyl) sulfonyl]amino]-1-H-indol-3-yl]propyl]-4-(5-methoxy-4-pyrimidinyl)piperazine (0.42 g, 0.8 mmol, 57%). The free base (0.42 g, 0.80 mmol) was dissolved in a minimum volume of acetonitrile. A concentrated solution of oxalic acid (0.072 g, 0.8 mmol) in CH$_3$CN was added with stirring. The precipitate was separated by filtration, washed sparingly with CH$_3$CN and dried at 70° C. in vacuo overnight to give the title compound (0.40 g, 0.66 mmol, 82%): mp 125°–127° C. Anal. Calcd for $C_{27}H_{32}N_6O_3S_1.1.0\ C_2H_2O_4$: C, 55.40; H, 5.77; N, 13.36. Found: C, 55.29; H, 5.41; N, 13.15.

EXAMPLE 59

1-[3-[5-[2-Pyrrolidinon-1-yl]-1H-indol-3-yl]propyl]-4-(5-methoxy-4-pyrimidinyl)piperazine oxalate To a mixture of 1-[3-[5-amino-1-H-indol-3-yl]propyl]-4-(5-methoxy-4-pyrimidinyl)piperazine (2.3g, 6.3 mmol), and sodium carbonate (0.67 g, 6.3 mmol) in 25 mL of acetone, cooled to 0° C., was added dropwise 4-chlorobutyryl chloride (0.89 g, 6.3 mmol). Additional acetone (10 mL) was added and the suspension was stirred for 19 h at 23° C. The insoluble material was separated by filtration and the acetone was removed in vacuo. The crude material was dissolved in EtOAc, and the solution was washed with water, dried (brine, MgSO$_4$), filtered, and concentrated in vacuo to give crude 1-[3-[5-[4-chlorobutyrylamino]-1-H-indol-3-yl]propyl]-4-(5-methoxy-4-pyrimidinyl)piperazine (1.98 g, 4.2 mmol, 67%) as a gum. Sodium ethoxide (0.67 mL, 2.1 mmol, 21% in ethanol) was added dropwise to a solution of crude 1-[3-[5-[4-chlorobutyrylamino]-1-H-indol-3-yl]propyl]-4-(5-methoxy-4-pyrimidinyl)piperazine (1.0 g, 2.1 mmol) in ethanol (5 mL). After the addition, the reaction mixture was heated at 78° C. for 90 min and then cooled to room temperature. The insoluble solid was separated and the filtrate was concentrated in vacuo. Silica gel column chromatography (95:5:0.5 $CH_2Cl_2$-MeOH-30% $NH_4OH$) afforded 1-[3-[5-[2-pyrrolidinone-1-yl]-1-yl]-1-H-indol-3-yl]propyl]-4-(5-methoxy-4-pyrimidinyl)piperazine (0.33 g, 0.76 mmol, 36%). The free base (0.25 g, 0.58 mmol) was dissolved in a minimum volume of acetonitrile. A concentrated solution of oxalic acid (0.052 g, 0.58 mmol) in CH$_3$CN was added with stirring. The precipitate was separated by filtration, washed sparingly with CH$_3$CN, and dried at 70° C. in vacuo overnight to give the title compound (0.17 g, 56%): mp 100°–101° C. Anal. Calcd for $C_{24}H_{30}N_6O_2.1.0\ C_2H_2O_4.1.15\ H_2O$: C, 57.26; H, 6.34; N, 15.41. Found: C, 56.90; H, 5.96; N, 15.51.

By appropriate modification of the foregoing synthetic examples, additional Formula 1 compounds may be obtained. Selected additional example compounds are set forth in Table 1.

TABLE 1

Additional Products of Formula I

[Structure I: indole with R¹(CH₂)ₙ and R² substituents, connected via chain with R³ to piperazine with R⁵, R⁶ substituents, attached to pyrimidine with OR⁴]

| Example No. | R¹ | n | R² | R³ | R⁴ | R⁵ | R⁶ | MP °C. of HCl salt (unless otherwise specified) |
|---|---|---|---|---|---|---|---|---|
| 60 | 5-F | 0 | H | H | Me | H | H | 119–122 (base) |
| 61 | H | 0 | H | H | Me | H | H | 221–224 |
| 62 | H | 0 | H | H | Me | H | Me | 185 (dec) |
| 63 | 5-MeSO₂NH | 0 | H | H | Me | H | H | 150–152 |
| 64 | 5-MeSO₂NMe | 0 | H | H | Me | H | Me | 205–206 |
| 65 | 5-MeSO₂NMe | 0 | H | H | Me | H | H | 227–230 |
| 66 | 5-MeSO₂NMe | 0 | H | H | Me | H | Me | 215–218 |
| 67 | 5-EtSO₂NH | 0 | H | H | Me | H | H | 140–145 |
| 68 | 5-EtSO₂NMe | 0 | H | H | Me | H | H | 223–225 |
| 69 | 5-EtSO₂NMe | 0 | H | H | Me | H | Me | 205–207 |
| 70 | 5-EtSO₂NH | 0 | H | H | Me | H | Me | 212–214 |
| 71 | 5-EtO | 0 | H | H | Me | H | H | 112–114 (base) |
| 72 | 5-PhCH₂O | 0 | H | H | Me | H | H | 180 (dec) |
| 73 | 5-MeO | 0 | H | H | Me | H | H | 130–150 (dec) |
| 74 | 5-F | 0 | 6-F | H | Me | H | H | 102–104 (base) |
| 75 | 4-F | 0 | 7-F | H | Me | H | H | 160–165 (base) |
| 76 | 5-F | 0 | 7-F | H | Me | H | H | >250 (dec) |
| 77 | 5-H₂NSO₂ | 1 | H | H | Me | H | H | 125–127 (succinate) |
| 78 | 5-H₂NCO | 1 | H | H | Me | H | H | 170 (dec) |
| 79 | 5-CN | 1 | H | H | Me | H | H | 163–165 (fumarate) |
| 80 | 5-PhCH₂NHCO | 1 | H | H | Me | H | H | 112–115 |
| 81 | 5-EtO₂C | 0 | H | H | Me | H | H | 215–216 |
| 82 | 5-MeO₂C | 0 | H | H | Me | H | H | — |
| 83 | 5-MeNHCO | 0 | H | H | Me | H | H | >215 |
| 84 | 5-EtNHCO | 0 | H | H | Me | H | H | >215 |
| 85 | 5-PhCH₂CH₂NHCO | 0 | H | H | Me | H | H | 155–165 |
| 86 | 5-PhCH₂NHCO | 0 | H | H | Me | H | H | 190–195 |
| 87 | 5-CHONH | 0 | H | H | Me | H | H | 118–119 (oxalate) |
| 88 | 5-CH₃CONH | 0 | H | H | Me | H | H | 135–137 (oxalate) |
| 89 | 5-F | 0 | H | H | Me | Me | H | 215–218 |
| 90 | 5-F | 0 | 6-CO₂Me | H | Me | H | H | 225–230 darkens |
| 91 | 5-F | 0 | 6-MeO | H | Me | H | H | 236–238 |

TABLE 2

5-HT$_{1D}$ Binding Site Affinities For Representative Formula I Compounds

| Example No. | 5-HT$_{1D}$ Binding IC$_{50}$ (nM) |
|---|---|
| 52 | 2.0 |
| 53 | 5.0 |
| 54 | 20.5 |
| 55 | 0.8 |
| 60 | 3.0 |
| 61 | 2.9 |
| 62 | 4.2 |
| 63 | 5.2 |
| 64 | 9.6 |
| 65 | 4.9 |
| 66 | 12.0 |
| 67 | 13.7 |
| 68 | 12.9 |
| 69 | 19.1 |
| 70 | 17.1 |
| 71 | 2.2 |
| 72 | 14.3 |
| 73 | 1.1 |
| 74 | 29.0 |
| 75 | 5.1 |
| 76 | 8.1 |

We claim:

1. A compound of Formula I or a pharmaceutically acceptable acid addition salt and/or solvate thereof

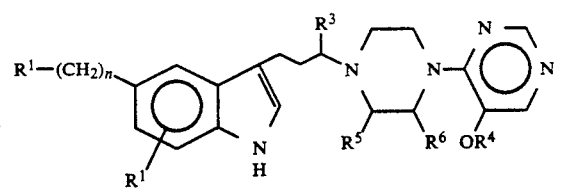

wherein
R¹ is a substituent selected from the group consisting of hydrogen, halogen, lower alkyl, lower alkoxy, R⁷-substituted phenyl-lower alkoxy, amino, cyano, hydroxy, nitro, —OCH₂CN, —OCH₂CONR⁷R⁸, —SO₂NR⁷R⁸, —O₂CR⁹, —SO₂R⁹, —O₂CNR⁷R⁸, —COR⁸, —CO₂R⁹, —CONR⁷R⁸, —NR⁷CO₂R⁹, —NR⁷COR⁸, —NR⁷SO₂R⁹ and

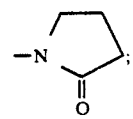

$R^2$ is selected from hydrogen, lower alkyl, lower alkoxy, $-CO_2R^9$ and halogen;

$R^3$ is independently selected from hydrogen and lower alkyl, with the proviso that $R^3$ cannot be hydrogen when the $R^1-(CH_2)_n$ moiety is hydrogen, lower alkyl, lower alkoxy, halogen or $-CONH_2$ and $R^2$ is hydrogen, lower alkyl and halogen;

$R^5$, $R^6$ and $R^7$ are independently selected from hydrogen and lower alkyl;

$R^4$ is lower alkyl;

$R^8$ is selected from hydrogen, lower alkyl, $R^7$-phenyl-lower alkyl and trifluoromethyl;

$R^9$ is selected from lower alkyl and $R^7$-phenyl-lower alkyl; and n is zero or the integers 1 or 2.

2. The compound of claim 1 wherein $R^1$ is selected from the group consisting of $-SO_2NR^7R^8$ and $-SO_2R^9$.

3. The compound of claim 1 wherein $R^1$ is selected from the group consisting of hydrogen, halogen, lower alkyl, lower alkoxy, $R^7$-phenyl-lower alkoxy, amino, cyano, hydroxy, and nitro.

4. The compound of claim 1 wherein $R^1$ is selected from the group consisting of $-OCH_2CN$, $-OCH_2CONR^7R^8$, $-O_2CR^9$ and $-O_2CNR^7R^8$.

5. The compound of claim 1 wherein $R^1$ is selected from the group consisting of $-COR^8$, $-CO_2R^9$ and $CONR^7R^8$.

6. The compound of claim 1 wherein $R^1$ is selected from the group consisting of $-NR^7SO_2R^9$, $-NR^7CO_2R^9$, $-NR^7COR^8$ and 7. The compound of claim 2, wherein $R^1$ is $-SO_2NR^7R^8$, selected from the group consisting of 4-(5-methoxy-4-pyrimidinyl)-1-[3-[5-[[(methylamino)-sulfonyl]methyl]-1H-indol-3-yl]propyl]piperazine; 4-(5-methoxy-4-pyrimidinyl)-1-[3-[5-[[(methylamino)sulfonyl]methyl]-1H-indol-3-yl]propyl]-3-methylpiperazine; and 1-[3-[5-[[(dimethylamino)sulfonyl]methyl]-1H-indol-3-yl]propyl]-4-(5-methoxy-4-pyrimidinyl)piperazine; and 1-[3-[5-[(aminosulfonyl)methyl]-1H-indol-3-yl]propyl]-4-(5-methoxy-4-pyrimidinyl)piperazine.

8. The compound of claim 2, wherein $R^1$ is $-SO_2R^9$, selected from the group consisting of 4-(5-methoxy-4-pyrimidinyl)-1-[3-[5-[2-(methylsulfonyl)methyl]-1H-indol-3-yl]propyl]-3-methylpiperazine; 4-(5-methoxy-4-pyrimidinyl)-1-[3-[5-[2-(methylsulfonyl)methyl]-1H-indol-3-yl]propyl]-3-methylpiperazine; 4-(5-methoxy-4-pyrimidinyl)-1-[3-[5-[2-(methylsulfonyl)ethyl]-1H-indol-3-yl]propyl]piperazine; and 4-(5-methoxy-4-pyrimidinyl)-1-[3-[5-[2-(methylsulfonyl)ethyl]-1H-indol-3-yl]propyl]-3-methylpiperazine.

9. The compound of claim 3 selected from the group consisting of 1-[3-(5-cyano-1H-indol-3-yl)propyl]-4-(5-methoxy-4-pyrimidinyl)piperazine; 1-[3-(5-cyano-1H-indol-3-yl)propyl]-4-(5-methoxy-4-pyrimidinyl)-3-methylpiperazine; 3-[3-[4-(5-methoxy-4-pyrimidinyl)-1-piperazinyl]-propyl]-5-nitroindole; 3-[3-[4-(5-methoxy-4-pyrimidinyl)-1-piperazinyl]propyl]-5-aminoindole; 1-[3-(1H-indol-3-yl)-3-methylpropyl]-4-(5-methoxy-4-pyrimidinyl)piperazine; 1-[3-(1H-indol-3-yl)propyl]-4-(5-methoxy-4-pyrimidinyl)-3-methylpiperazine; 1-[3-(5-hydroxy-1H-indol-3-yl)propyl]-4-(5-methoxy-4-pyrimidinyl)piperazine; 3-[3-[4-(5-methoxy-4-pyrimidinyl)-1-piperazinyl]-3-ethylpropyl]indole; 1-[3-(5-phenylmethoxy-1H-indol-3-yl)propyl]-4-(5-methoxy-4-pyrimidinyl)piperazine; 3-[3-[4-(5-methoxy-4-pyrimidinyl)-1-piperazinyl]propyl]-5-fluoro-6-acetoxyindole; and 3-[3-[4-(5-methoxy-4-pyrimidinyl-1-piperazinyl]propyl]-5-fluoro-6-methoxyindole.

10. The compound of claim 4 selected from the group consisting of 3-[3-[4-(5-methoxy-4-pyrimidinyl)-1-piperazinyl]propyl]-5-(cyanomethyl)oxyindole and 3-[3-[4-(5-methoxy-4-pyrimidinyl)-1-piperazinyl]propyl]-5-(carboxamidomethyl)oxyindole.

11. The compound of claim 5 selected from the group consisting of 1-[3-(5-aminocarbonyl-1H-indol-3-yl)propyl]-4-(5-methoxy-4-pyrimidinyl)-3-methylpiperazine; 1-[3-[5-acetyl-1H-indol-3-yl]propyl]-4-(5-methoxy-4-pyrimidinyl)piperazine; 1-[3-[5-[(aminocarbonyl) methyl]-1H-indol-3-yl]propyl]-4-(5-methoxy-4-pyrimidinyl)piperazine; 4-(5-methoxy-4-pyrimidinyl)-1-[3-[5-[[(phenylmethylamino)carbonyl]methyl]-1H-indol-3-yl]propyl]piperazine; 1-[3-[5-(ethoxycarbonyl)-1H-indol-3-yl]propyl]-4-(5-methoxy-4-pyrimidinyl) piperazine; 1-[3-[5-(methoxycarbonyl)-1H-indol-3-yl]propyl]-4-(5-methoxy-4-pyrimidinyl) piperazine; 4-(5-methoxy-4-pyrimidinyl)-1-[3-[5-[(methylamino) carbonyl]-1H-indol-3-yl]propyl]piperazine; 1-[3-[5-[(ethylamino)carbonyl]-1H-indol-3-yl]propyl]-4-(5-methoxy-4-pyrimidinyl)piperazine; 1-[3-[5-[(n-butylamino)carbonyl]-1H-indol-3-yl]propyl]-4-(5-methoxy-4-pyrimidinyl)piperazine; 4-(5-methoxy-4-pyrimidinyl)-1-[3-[5-[[1-(2-phenylethyl) amino]carbonyl]-1H-indol-3-yl]propyl]piperazine; and 4-(5-methoxy-4-pyrimidinyl)-1-[3-[5-[[(phenylmethyl)amino]carbonyl]-1H-indol-3-yl]propyl]piperazine.

12. The compound of claim 6 wherein $R^1$ is $-NR^7SO_2R^9$, selected from the group consisting of 4-(5-methoxy-4-pyrimidinyl)-1-[3-[5-[methyl(methylsulfonyl)amino]-1-H-indol-3-yl]propyl]-2-methylpiperazine; 4-(5-methoxy-4-pyrimidinyl)-1-[3-[5-[(methylsulfonyl)amino]-1-H-indol-3-yl]propyl]-2-methylpiperazine;1-[[5-[[(ethylsulfonyl)amino]-methyl]-1H-indol-3-3-yl]propyl]-4-(5-methoxy-4-pyrimidinyl)-3-methylpiperazine; 1-[3-[5-[(ethylsulfonyl)amino]-1H-indol-3-yl]propyl]-4-(5-methoxy-4-pyrimidinyl)-2-methylpiperazine; 1-[[5-[[ethylsulfonyl)amino]methyl]-1H-indol-3-yl]propyl]-4-(5-methoxy-4-pyrimidinyl)-2-methylpiperazine; 1-[[5-[[(ethylsulfonyl)amino]methyl]-1H-indol-3-yl]propyl]-4-(5-methoxy-4-pyrimidinyl)piperazine; 4-(5-methoxy-4-pyrimidinyl)-1-[3-[5-[methyl(ethylsulfonyl)amino]-1H-indol-3-yl]propyl]-2-methylpiperazine; 4-(5-methoxy-4-pyrimidinyl)-1-[[5-[[(methylsulfonyl)amino]methyl]-1H-indol-3-yl]propyl]piperazine; 1-[[5-[[(methylsulfonyl)amino]methyl]-1H-indol-3-yl]propyl]-4-(5-methoxy-4-pyrimidinyl)-3-methylpiperazine; 1-[[5-[[ethyl(methylsulfonyl)amino]-methyl]-1H-indol-3-yl]propyl]-4-(5-methoxy-4-pyrimidinyl) piperazine; 4-(5-methoxy-4-pyrimidinyl)-1-[[5-[[methyl(ethylsulfonyl)amino]methyl]-1H-indol-3-yl]propyl]piperazine; 4-(5-methoxy-4-pyrimidinyl)-1-[[5-[[phenylmethyl(ethylsulfonyl)amino]-methyl]-1H-indol-3-yl]propyl]piperazine; 4-(5-methoxy-4-pyrimidinyl)-1-[[5-[[phenylmethyl(methylsulfonyl)amino]methyl]-1H-indol-3-yl] propyl]piperazine; 4-(5-methoxy-4-pyrimidinyl)-1-[[5-[[methyl(methylsulfonyl)amino]methyl]-1H-indol-3-yl]propyl] piperazine; 4-(5-methoxy-4-pyrimidinyl)-1-[3-[5-[methyl(trifluoromethylsulfonyl)amino]-1H-indol-3-yl]propyl]piperazine; 1-[3-(5-methylsulfonyl)amino-1H-indol-3-yl)propyl]-4-(5-methoxy-4-pyrimidinyl) piperazine; 1-[3-[5-(methylsulfonyl)amino-1H-indol-3-yl)propyl]-4-(5-methoxy-4-pyrimidinyl)-3-methylpiperazine; 1-[3-[5-(ethylsulfonyl)amino-1H-indol-3-yl)propyl]-4-(5-methoxy-4-pyrimidinyl) piperazine; 1-[3-[5-(ethylsulfonyl)methylamino-1H- indol-3-yl]propyl]-4-(5-methoxy-4-pyrimidinyl) piperazine; 1-[3-[5-(ethylsulfonyl)amino-1H-indol-3-yl]propyl]-4-(5-methoxy-4-pyrimidinyl)-3-methylpiperazine; and 1-[3-[5-[[(4-methylphenyl) sulfonyl]amino]-1H-indol-3-yl]propyl]-4-(5-methoxy-4-pyrimidinyl)piperazine.

13. The compound of claim 6, wherein $R^1$ is —NR$^7$COR$^8$, selected from the group consisting of 1-[[5-[[(acetyl)amino]methyl]-1H-indol-3-yl]propyl]-4-(5-methoxy-4-pyrimidinyl)piperazine; 1-[3-[5-formylamino-1H-indol-3-yl]propyl]-4-(5-methoxy-4-pyrimidinyl)piperazine; 1-[3-[5-acetylamino-1H-indol-3-yl]propyl]-4-(5-methoxy-4-pyrimidinyl)piperazine; and 1-[3-[5-[(trifluoromethyl)carbonyl]amino-1H-indol-3-yl]propyl]-4-(5-methoxy-4-pyrimidinyl)piperazine.

14. The compound of claim 6 selected from the group consisting of 1-[3-[5-[[(phenylmethoxy)carbonyl]amino]-1H-indol-3-yl]propyl]-4-(5-methoxy-4-pyrimidinyl)piperazine; 1-[3-[5-[[(methoxy)carbonyl]amino]-1H-indol-3-yl]propyl]-4-(5-methoxy-4-pyrimidinyl)piperazine; and 1-[3-[5-[2-pyrrolidinon-1-yl]-1H-indol-3-yl]propyl]-4-(5-methoxy-4-pyrimidinyl)piperazine 15. The compound of claim 7, 4-(5-methoxy-4-pyrimidinyl)-1-[3-[5-[[(methylamino)sulfonyl]methyl]-1H-indol-3-yl]propyl]piperazine.

16. A method for treating vascular headaches, comprising migraine and cluster headaches, by administering a therapeutically effective amount of a Formula XXI compound or a pharmaceutically acceptable salt and/or solvate thereof to a person suffering from the vascular headache,

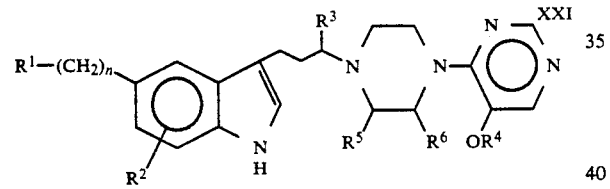

wherein
$R^1$ is a substituent selected from the group consisting of hydrogen, halogen, lower alkyl, lower alkoxy, $R^7$-substituted phenyl-lower alkoxy, amino, cyano, hydroxy, nitro, —OCH$_2$CN, —OCH$_2$CONR$^7$R$^8$, —SO$_2$NR$^7$R$^8$, —O$_2$CR$^9$, —SO$_2$R$^9$, —O$_2$CNR$^7$R$^8$, —COR$^8$, —CO$_2$R$^9$, —CONR$^7$R$^8$, —NR$^7$CO$_2$R$^9$, —NR$^7$COR$^8$, —NR$^7$SO$_2$R$^9$ and

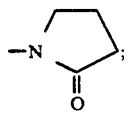

$R^2$ is selected from hydrogen, halogen, lower alkyl, lower alkoxy and —CO$_2$R$^9$;
$R^3$, $R^5$, $R^6$ and $R^7$ are independently selected from hydrogen and lower alkyl;
$R^4$ is lower alkyl;
$R^8$ is selected from hydrogen, lower alkyl, $R^7$-phenyl-lower alkyl and trifluoromethyl;
$R^9$ is selected from lower alkyl and $R^7$-phenyl-lower alkyl; and
n is zero or the integers 1 or 2.

17. A method for preventing vascular headaches, comprising migraine and cluster headaches, by administering a prophylactically effective amount of a Formula XXI compound or a pharmaceutically acceptable salt and/or solvate thereof to a person at risk of suffering the onset of a vascular headache,

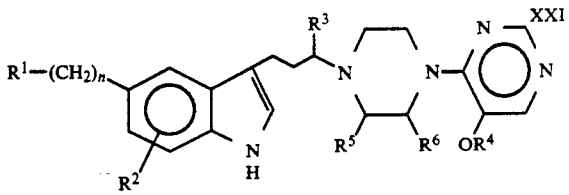

wherein
$R^1$ is a substituent selected from the group consisting of hydrogen, halogen, lower alkyl, lower alkoxy, $R^7$-substituted phenyl-lower alkoxy, amino, cyano, hydroxy, nitro, —OCH$_2$CN, —OCH$_2$CONR$^7$R$^8$, —SO$_2$NR$^7$R$^8$, —O$_2$CR$^9$, —SO$_2$R$^9$, —O$_2$CNR$^7$R$^8$, —COR$^8$, —CO$_2$R$^9$, —CONR$^7$R$^8$, —NR$^7$CO$_2$R$^9$, —NR$^7$COR$^8$, —NR$^7$SO$_2$R$^9$ and

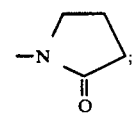

$R^2$ is selected from hydrogen, halogen, lower alkyl, lower alkoxy and —CO$_2$R$^9$;
$R^3$, $R^5$, $R^6$ and $R^7$ are independently selected from hydrogen and lower alkyl;
$R^4$ is lower alkyl;
$R^8$ is selected from hydrogen, lower alkyl, $R^7$-phenyl-lower alkyl and trifluoromethyl;
$R^9$ is selected from lower alkyl and $R^7$-phenyl-lower alkyl; and
n is zero or the integers 1 or 2.

18. A pharmaceutical composition in unit dosage form suitable for systemic administration to a person at risk of or suffering a vascular headache, the composition comprising a pharmaceutical carrier and from about 1 to 500 mg of a Formula XXI compound or a pharmaceutically acceptable salt and/or solvate thereof, which Formula XXI compound is:

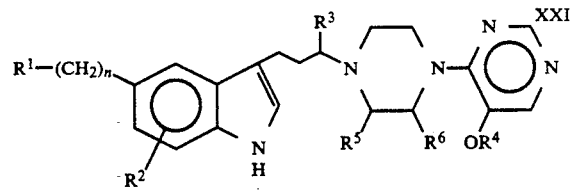

wherein
$R^1$ is a substituent selected from the group consisting of hydrogen, halogen, lower alkyl, lower alkoxy, $R^7$-substituted phenyl-lower alkoxy, amino, cyano, hydroxy, nitro, —OCH$_2$CN, —OCH$_2$CONR$^7$R$^8$, —SO$_2$NR$^7$R$^8$, —O$_2$CR$^9$, —SO$_2$R$^9$, —O$_2$CNR$^7$R$^8$, —COR$^8$, —CO$_2$R$^9$, —CONR$^7$R$^8$, —NR$^7$CO$_2$R$^9$, —NR$^7$COR$^8$, —NR$^7$SO$_2$R$^9$ and

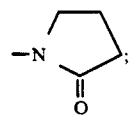
R² is selected from hydrogen, halogen, lower alkyl, lower alkoxy and —CO₂R⁹.
R³, R⁵, R⁶ and R⁷ are independently selected from hydrogen and lower alkyl;
R⁴ is lower alkyl;
R⁸ is selected from hydrogen, lower alkyl, R⁷-phenyl-lower alkyl and trifluoromethyl;
R⁹ is selected from lower alkyl and R⁷-phenyl-lower alkyl; and
n is zero or the integers 1 or 2.
* * * * *

UNITED STATES PATENT AND TRADEMARK OFFICE
CERTIFICATE OF CORRECTION

PATENT NO.: 5,300,506
DATED      : April 5, 1994
INVENTOR(S): David W. Smith et al Page 1 of 2

It is certified that error appears in the above-identified patent and that said Letters Patent is hereby corrected as shown below:

In the Abstract and in column 47, in claim 1, $R^2$ has been designated $R^1$; therefore the structure at line 48 structure should be as follows:

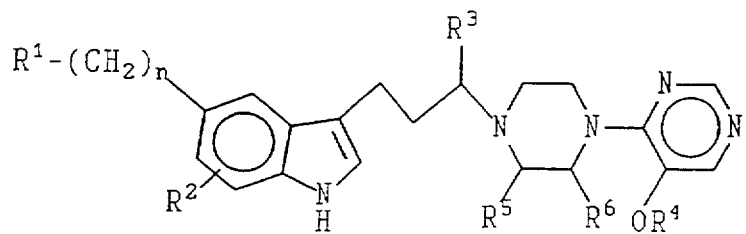

I

UNITED STATES PATENT AND TRADEMARK OFFICE
CERTIFICATE OF CORRECTION

PATENT NO. : 5,300,506

DATED : April 5, 1994

INVENTOR(S) : David W. Smith, et al.

It is certified that error appears in the above-indentified patent and that said Letters Patent is hereby corrected as shown below:

In column 47, line 32, claim 6, please add the following omitted structure after the word "and"

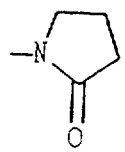

Signed and Sealed this

Ninth Day of August, 1994

Attest:

BRUCE LEHMAN

*Attesting Officer*   *Commissioner of Patents and Trademarks*